US006495664B1

(12) United States Patent
Cubitt

(10) Patent No.: US 6,495,664 B1
(45) Date of Patent: Dec. 17, 2002

(54) FLUORESCENT PROTEIN SENSORS OF POST-TRANSLATIONAL MODIFICATIONS

(75) Inventor: Andrew B. Cubitt, San Diego, CA (US)

(73) Assignee: Aurora Biosciences Corporation, San Diego, CA (US)

( * ) Notice: Subject to any disclaimer, the term of this patent is extended or adjusted under 35 U.S.C. 154(b) by 0 days.

(21) Appl. No.: 09/129,192

(22) Filed: Jul. 24, 1998

(51) Int. Cl.⁷ .......................... C07K 1/00; A61K 38/00; C12Q 1/00
(52) U.S. Cl. .................... 530/350; 530/300; 435/4
(58) Field of Search ........................ 435/6, 7.1; 436/501

(56) References Cited

U.S. PATENT DOCUMENTS

| | | | |
|---|---|---|---|
| 4,314,936 A | 2/1982 | Yaron et al. | 260/112.5 R |
| 5,264,563 A | 11/1993 | Huse | 536/25.3 |
| 5,314,936 A | 5/1994 | Schwartz et al. | 524/82 |
| 5,491,084 A | 2/1996 | Chalfie et al. | 435/189 |
| 5,599,906 A | 2/1997 | Dasmahapatra | 530/350 |
| 5,602,021 A | 2/1997 | Davis et al. | 435/219 |
| 5,605,809 A | 2/1997 | Komoriya et al. | 435/23 |
| 5,614,191 A | 3/1997 | Puri et al. | 424/178.1 |
| 5,625,048 A | 4/1997 | Tsien et al. | 536/23.4 |
| 5,777,079 A | 7/1998 | Tsien et al. | 530/350 |
| 5,804,387 A | 9/1998 | Cormack et al. | 435/6 |
| 5,912,137 A * | 6/1999 | Tsien et al. | 435/15 |
| 5,925,558 A * | 7/1999 | Tsien et al. | 435/252.3 |

FOREIGN PATENT DOCUMENTS

| | | |
|---|---|---|
| EP | 0 428 000 A1 | 5/1991 |
| WO | WO 91/01305 | 2/1991 |
| WO | WO 94/28166 | 12/1994 |
| WO | WO 94/28173 | 12/1994 |
| WO | WO 95/21191 | 8/1995 |
| WO | WO 96/13607 | 5/1996 |
| WO | WO 96/23810 | 8/1996 |
| WO | WO 96/23898 | 8/1996 |
| WO | WO 96/27027 | 9/1996 |
| WO | WO 96/27675 | 9/1996 |
| WO | WO 97/11094 | 3/1997 |
| WO | WO 97/28261 | 8/1997 |
| WO | WO 97/42320 | 11/1997 |
| WO | WO 98/36099 | 2/1998 |
| WO | WO 98/21355 | 5/1998 |
| WO | WO 98/30715 | 7/1998 |
| WO | WO 98/32879 | 7/1998 |

OTHER PUBLICATIONS

Hanson, PI and Schulman, H. (1992) Annu. Rev. Biochem. 61 pp. 586–587 Neuronal CA2+/calmodulin–dependent protein kinases.*
Wilkinson, S.E. and Hallam, T.J. (1994) Trends Pharmacol. Sci. 15(2) 53–7 Protein kinase C: is its pivotal role in cellular activation over stated?.*
Woodgett, JR. (1991) Methods Enzymol. 200, 169–178 Use of synthetic peptides mimicking phosphorylation sites for affinity purification of protein –serine kinases.*

(List continued on next page.)

Primary Examiner—Ardin H. Marschel
(74) Attorney, Agent, or Firm—Gray Cary Ware & Friedenrich LLP; Lisa A. Haile

(57) ABSTRACT

The present invention includes a fluorescent compound that can detect an activity, such as an enzymatic activity, and exhibits quenching. The fluorescent compound can include a fluorescent protein, such as an Aequorea-related green fluorescent protein. The fluorescent compound can include a substrate site for an enzymatic activity such as a kinase activity, a phosphatase activity, a protease activity, and a glycosylase activity. The fluorescent compound of the present invention can be used to detect such enzymatic activities in samples, such as biological samples, including cells. The present invention also includes nucleic acids that encode the fluorescent compounds of the present inventions, and cells that include such nucleic acids or fluorescent compounds.

23 Claims, 10 Drawing Sheets

OTHER PUBLICATIONS

Baldwin et al., Biochemistry 29:5509–9915 (1990).
Beaudette et al., Journal of Biological Chemistry vol. 268, No. 28, Oct. 1993 pp. 20825–20830.
Blondel et al., Protein Engineering 4:457–461 (1991).
Bouvier et al., Methods Enzymol. 248:614–633 (1995).
Branchini et al., Journal of The American Chemical Society, vol. 120, No. 1, pp. 1–6 (1998).
Cartwright et al., Yeast 10:497–508 (1994).
Chalfie et al., Science 263:802–805 (1994).
Cheng et al., Nature Biotechnology 14:606–609 (May 1996).
Clarke, Current Biology, vol. 4, No. 7, 1994, pp. 647–650.
Cody et al., Biochemistry 32:1212–1218 (1993).
Colbran et al, J. Biol. Chem. 267:9589–9594 (1995).
Creamer et al., Protein Science 1995, vol. 4, pp. 1305–1314.
Cubitt et al., Trands in Biochem. Sci . 20:448–455 (1995).
Dale et al., FEBS Letters 361 (1995) pp. 191–195.
Dekker et al., TIBS, Feb. 1994, pp. 73–77.
Delagrave et al., Bio/Technology 13:151–154 (1995).
Denis et al., The Journal of Biological Chemistry, 1991, pp. 17932–17935, vol. 266, No. 27.
Deschamps et al., Protein Expression and Purification, 6:555–558 (1995).
Dunn et al., Meth. Enzymol. (1994), vol. 241, pp 254–279.
Ehrig et al., FEBS Letters 367:163–166 (1995).
Erickson et al., The Journal of Biological Chemistry, pp. 19728–19735, vol. 265, No. 32, (1990).
Feil et al., Molecular and Cellular Biochemistry 1993, pp. 71–80, vol. 127/128.
Forood et al., Proc. Natl. Acad. Sci. USA, Feb. 1993, pp. 838–842, vol. 90.
Fujise et al., The Journal of Biological Chemistry, vol. 269, No. 50, Dec. 16, 1994, pp. 31642–31648.
Gonzalez et al., The Journal of Biological Chemistry, vol. 266, No. 33, Nov. 25, 1991, pp. 22159–22163.
Graff et al., J. Biol. Chem. 266:14390–14398 (1991).
Hardy et al., "Amyloid protein precursor in development, aging, and Alzheimer's disease" ed.,C.L. Masters et al., pp. 190–198 (1994).
Heim et al., Proc. Natl. Acad. Sci. U.S.A. 91:12501–12505 (1994).
Heim et al., Nature 373:663–664 (1995).
Heim et al., Current Biology 6:178–182 (Feb. 1996).
Hurley et al., Science, vol. 249, Aug. 1990, pp. 1012–1016.
Inouye et al., FEBS Letters, 1994, pp. 211–214, vol. 351.
Kain et al., Biotechniques 19:650–55 Oct. 1995.
Kemp et al., Trends Biochem. Sci. 15:342–346 (1990).
Kemp et al., Methods in Enzymology, vol. 200 1991, pp. 121–156.
Knight, Methods Enzymol. 248:18–34 (1995).
Krafft et al., Methods Enzymol, 241:70–86 (1994).
Kwon et al., The Journal of Biological Chemistry, vol. 269 No. 7, pp. 4839–4844 (1994).
Lee et al., Proc. Natl. Acad Sci. U.S.A. 91:6413–6417 (1994).
Levine et al., Comp. Biochem. Physiol. 72B:77–85 (1982).
Li et al., Proc. Natl. Acad. Sci. USA vol. 86, pp. 558–562, Jan. 1989.
Lim et al., J. Biochem 118, 13–17, 1995.
Lindberg et al., TIBS Mar. 1992 pp. 114–119.
Lu et al., The Journal of Biological Chemistry vol. 269, No. 9, pp. 6603–6607, 1994.
Malencik et al., Analytical Biochemistry 132,34–40 1983.
Matayoshi et al., Science 247 (1990) pp 954–958.
Mitra et al., Gene, 173:13–17 (1996).
Mitchell et al., Biochemistry 1995, 34, 528–34.
Muhlrad et al., Yeast 8:79–82 (1992).
Munoz et al., J. Mol. Biol 1995, pp. 275–296.
Munoz et al., Current Opinion in Biotechnology 1995, 6:382–86.
Nakai et al., J. Biochem 104:693–699 1988.
Nishikawa et al., The Journal of Biological Chemistry vol. 272, No. 2, Jan. 10, pp. 952–960 1997.
Norris et al., Plant Molecular Biology, 24:673–677 (1994).
Onorato et al., Biochemistry 1991 30:5118–5125.
Patrick et al., DDT vol. 1, No. 8, Aug. 1996, pp. 325–330.
Parker et al., DukEngineer Fall 1997.
Pearson et al., Methods in Enzymology, vol. 200 pp. 62–81 1991.
Pearson et al., The Journal of Biochemistry vol. 260 No. 27 pp. 14471–14476, 1985.
Prasher et al., Gene 111:229–233 (1992).
Premont et al., The FASEB Journal Feb. 1995 vol. 9 pp. 175–182.
Prendergast et al., American Chemical Society, vol. 17 No. 17 1978 pp. 3448–3453.
Pullen et al., Protein Science 1995 4:2478–2486.
QI et al., The Journal of Biological Chemistry, vol. 270, No. 18 pp. 10847–10854, 1995.
Sala–Newby et al., Biochem J. 1991, 279, 727–732.
Seidah et al., Methods Enzymol. 244: (1994), pp. 175–188.
Shymko et al., Biochem J. 1997 326:463–69.
Smith et al., Methods Enzymol 244: (1994), pp 412–423.
Songyang et al., current Biology 4:973–982 (1994).
Songyang et al., Molecular and Cellular Biology Nov. 1996 pp. 6486–6493.
Sprang et al., Nature, vol. 336, (1988), pp 215–221.
Sterk et al., Journal of Fluorescence, vol. 7, No. 1 1997 (Supplemental) pp. 115–s118s.
Stokoe et al., Biochem. J. 296:843–849 (1993).
Stryer, Ann. Rev. Biochem. 47:819–846 (1978).
Swaminathan et al., Biophysical Journal vol. 72 Apr. 1997, pp. 1900–1907.
Szilak et al., Protein Science 1997, 6:1273–83.
Thornberry, Methods Enzymol, 244 (1994), pp 615–631.
Tsien et al., Handbook Of Biological Confocal Microscopy 1990 pp. 169–178.
Tsien et al., trends Cell. Biol. 3:242–245 (1993).
Ward et al., The Journal of Physical Chemistry vol. 80 No. 20 1976, 2289–2291.
Ward, in Bioluminescence and Chemiluminescence (eds. DeLuca et al., 235–242 (Academic Press, New York, 1981)).
Ward et al., Biochemistry 21:4535–4540 (1982).
Ward et al., Photochem. Photobiol. 35:803–808 (1982).
Wilbanks et al., J. Biol. Chem. 268:1226–1235 (1993).
Wright et al., Proc. Natl. Acad. Sci. USA vol. 78, No. 10, pp. 6048–6050, 1981.
Yang et al., The Journal Of Biological Chemistry vol. 269, No. 47 pp. 29855–29859 1994.
Yaron et al., Analytical Biocehm. 95:228–235 (1979).
Yokoe et al., Nature Biotechnology vol. 14, Oct. 1996 pp. 1252–1256.
Zhang et al., Nature vol. 367 24 1994, pp. 704–711.
Zhang et al., Biochemistry 1994, 33, pp. 2285–2290.
Zhang et al., Archives of Biochemistry and Biophysics vol. 315, No. 2 Dec. 1994 pp. 415–424.
Zhao et al., Biochem Biophys. Res. Comm 1991 vol. 176, No. 9 pp. 1454–1461.
Zhou et al., J. Am. Chem. Soc. 1994 116, 1139–1140.

* cited by examiner

SEQ ID NO:1:
SEQ ID NO:2:

(xi) SEQUENCE DESCRIPTION:

```
ATG AGT AAA GGA GAA CTT TTC ACT GGA GTT GTC CCA ATT CTT GTT     48
Met Ser Lys Gly Glu Leu Phe Thr Gly Val Val Pro Ile Leu Val
  1               5                  10                  15

GAA TTA GAT GGT GAT GTT AAT GGG CAC AAA TTT TCT GTC AGT GGA GAG     96
Glu Leu Asp Gly Asp Val Asn Gly His Lys Phe Ser Val Ser Gly Glu
             20                  25                  30

GGT GAA GGT GAT GCA ACA TAC GGA AAA CTT ACC CTT AAA TTT ATT TGC    144
Gly Glu Gly Asp Ala Thr Tyr Gly Lys Leu Thr Leu Lys Phe Ile Cys
         35                  40                  45

ACT ACT GGA AAA CTA CCT GTT CCA TGG CCA ACA CTT GTC ACT ACT TTC    192
Thr Thr Gly Lys Leu Pro Val Pro Trp Pro Thr Leu Val Thr Thr Phe
     50                  55                  60

TCT TAT GGT GTT CAA TGC TTT TCA AGA TAC CCA GAT CAT ATG AAA CGG    240
Ser Tyr Gly Val Gln Cys Phe Ser Arg Tyr Pro Asp His Met Lys Arg
 65                  70                  75                  80

CAT GAC TTT TTC AAG AGT GCC ATG CCC GAA GGT TAT GTA CAG GAA AGA    288
His Asp Phe Phe Lys Ser Ala Met Pro Glu Gly Tyr Val Gln Glu Arg
                 85                  90                  95

ACT ATA TTT TTC AAA GAT GAC GGG AAC TAC AAG ACA CGT GCT GAA GTC    336
Thr Ile Phe Phe Lys Asp Asp Gly Asn Tyr Lys Thr Arg Ala Glu Val
            100                 105                 110

AAG TTT GAA GGT GAT ACC CTT GTT AAT AGA ATC GAG TTA AAA GGT ATT    384
Lys Phe Glu Gly Asp Thr Leu Val Asn Arg Ile Glu Leu Lys Gly Ile
        115                 120                 125
```

FIG. 1A

```
GAT TTT AAA GAA GAT GGA AAC ATT CTT GGA CAC AAA TTG GAA TAC AAC    432
Asp Phe Lys Glu Asp Gly Asn Ile Leu Gly His Lys Leu Glu Tyr Asn
130                     135                     140

TAT AAC TCA CAC AAT GTA TAC ATC ATG GCA GAC AAA CAA AAG AAT GGA    480
Tyr Asn Ser His Asn Val Tyr Ile Met Ala Asp Lys Gln Lys Asn Gly
        145                     150                     155                     160

ATC AAA GTT AAC TTC AAA ATT AGA CAC AAC ATT GAA GAT GGA AGC GTT    528
Ile Lys Val Asn Phe Lys Ile Arg His Asn Ile Glu Asp Gly Ser Val
            165                     170                     175

CAA CTA GCA GAC CAT TAT CAA CAA AAT ACT CCA ATT GGC GAT GGC CCT    576
Gln Leu Ala Asp His Tyr Gln Gln Asn Thr Pro Ile Gly Asp Gly Pro
                180                     185                     190

GTC CTT TTA CCA GAC AAC CAT TAC CTG TCC ACA CAA TCT GCC CTT TCG    624
Val Leu Leu Pro Asp Asn His Tyr Leu Ser Thr Gln Ser Ala Leu Ser
                    195                     200                     205

AAA GAT CCC AAC GAA AAG AGA GAC CAG ATG GTC CTT CTT GAG TTT GTA    672
Lys Asp Pro Asn Glu Lys Arg Asp Gln Met Val Leu Leu Glu Phe Val
                        210                     215                     220

ACA GCT GCT GGG ATT ACA CAT GGC ATG GAT GAA CTA TAC AAA TA         717
Thr Ala Ala Gly Ile Thr His Gly Met Asp Glu Leu Tyr Lys
                            225                     230                     235
```

FIG. 1B

```
ATG AGT AAA GGA GAA GAA CTT TTC ACT GGA GTT GTC CCA ATT CTT GTT GAA TTA GAT GGT
Met Ser Lys Gly Glu Glu Leu Phe Thr Gly Val Val Pro Ile Leu Val Glu Leu Asp Gly
                    20                          40                          60
                                (His Lys)*                                       120

GAT GTT AAT GGG AGA AGA TTT TCT GTC AGT GGA GAG GGT GAA GGT GAT GCA ACA TAC GGA
Asp Val Asn Gly Arg Arg Phe Ser Val Ser Gly Glu Gly Glu Gly Asp Ala Thr Tyr Gly
                    80                          100                         180
                    Arg Arg                    140                160

AAA CTT ACC CTT AAA TTT ATT TGC ACT ACT GGA AAA CTA CCT GTT CCA TGG CCA ACA CTT
Lys Leu Thr Leu Lys Phe Ile Cys Thr Thr Gly Lys Leu Pro Val Pro Trp Pro Thr Leu
                    140                         200                         240
                                (Gln Cys)*                220

GTC ACT ACT TTC TCT TAT GGT GTT AGA AGA TTT TCA GCA TAC CCA GAT CAT AGT AAA CAG
Val Thr Thr Phe Ser Tyr Gly Val Arg Arg Phe Ser Ala Tyr Pro Asp His Met Lys Gln
                    200                                 280                     300
                                (Arg)*              *(Glu)

CAT GAC TTT TTC AAG AGT GCC ATG CCC GAA GGT TAT GTA CAG GTT CAG AGA AGA TCT ATA TTT TTC
His Asp Phe Phe Lys Ser Ala Met Pro Glu Gly Tyr Val Gln Val Gln Arg Arg Ser Ile Phe Phe
                    260                         320                         340

AAA GAT GAC GGG AAC TAC AAG ACA CGT GCT GAA GTC AAG TTT GAA GGT GAT ACC CTT GTT
Lys Asp Asp Gly Asn Tyr Lys Thr Arg Ala Glu Val Lys Phe Glu Gly Asp Thr Leu Val
```

FIG. 2A

```
                          380                   400                   420
                           *        (Asn)        *                     *
                                             (Glu Asp)*
AAT AGA ATC GAG TTA AAA GGT ATT GAT TTT AAA AGA AGA GGA AAC ATT CTT GGA CAC AAA
Asn Arg Ile Glu Leu Lys Gly Ile Asp Phe Lys Arg Arg Gly Ser Ile Leu Gly His Lys
                          440                   460                   480
                           *                     *        (Gln) (Asn)  *
TTG GAA TAC AAC TAT AAC TCA CAC AAT GTA TAC ATG GCA GAC AAA AGA AAG TCT GGA
Leu Glu Tyr Asn Tyr Asn Ser His Asn Val Tyr Met Ala Asp Lys Arg Lys Ser Gly
                          500                   520                   540
                           *                     *                     *
                                             (Glu Asp)*
ATC AAA GTT AAC TTC AAA ATT AGA CAC AAC ATT AGA AGA AGC GTT CAA CTA GCA GAC
Ile Lys Val Asn Phe Lys Ile Arg His Asn Ile Arg Arg Gly Ser Val Gln Leu Ala Asp
                          560                   580                   600
                           *                     *              (His Tyr)
CAT TAT CAA CAA AAT ACT CCA ATT GGC GAT GGC CCT GTC CTT TTA CCA GAC AAC AGA AGA
His Tyr Gln Gln Asn Thr Pro Ile Gly Asp Gly Pro Val Leu Leu Pro Asp Asn Arg Arg
                          620                   640                   660
                           *                     *    (His)            *
CTG TCC ATA CAA TCT GCC CTT TCG AAA GAT CCC AAC GAA AAG AGA GAC AGA ATG GTC CTT
Leu Ser Ile Gln Ser Ala Leu Ser Lys Asp Pro Asn Glu Lys Arg Asp Arg Met Val Leu
    (Thr)                 680                   700
                           *                     *
CTT GAG TTT GTA ACA GCT GCT GGG ATT ACA CAT GGC ATG GAT GAA CTA TAC AAA TAA
Leu Glu Phe Val Thr Ala Ala Gly Ile Thr His Gly Met Asp Glu Leu Tyr Lys ***
```

FIG. 2B

FLUORESCENT PROTEIN SENSORS OF POST-TRANSLATIONAL MODIFICATIONS

TECHNICAL FIELD

The present invention generally relates to compositions and methods for the detection of activities, such as enzymatic activities, using fluorescent compounds that are modified by the activity such that they exhibit a change in their sensitivity to quenching.

BACKGROUND

Fluorescent compounds have been used in the art to detect a wide variety of biological phenomenon, such as changes in ion concentration, specific binding reactions, subcellular localization, and enzymatic reactions. In the case of detecting changes in ion concentration, specific binding reactions, and subcellular localization, the fluorescent compound is used as a label to detect such specific binding or localization. In some cases, the fluorescence of the fluorescent compound is altered after an enzyme has acted on the fluorescent compound or a molecule binds with the fluorescent compound. For example, the activity of beta-galactosidase on the substrate fluorescein di-beta-D-galactopyranoside causes an increase in fluorescence of the substrate (Molecular Probes Catalogue, Sixth Edition, p.208 (1996)). Likewise, the action of beta-lactamase on CCF2-AM causes the compound to change fluorescence from green to blue due to an uncoupling of fluorescence resonance energy transfer (FRET) (Tsien and Zlokarnik, WO 96/30540, published Oct. 3, 1996). Protease activity can also be detected by the action of a protease on a fluorescent compound that uncouples FRET of the fluorescent compound (Tsien et al., WO 97/28261, published Aug. 7, 1997).

The detection of enzymatic reactions is important for the study of biological phenomenon, cellular biology, medical diagnostics, and drug discovery. Several classes of enzymes have been implicated in disease states, such as proteases for HIV and kinases for cancer. Drug discovery preferably uses living cells to detect compounds that can alter the activity enzymes involved in such disease states. However, ex vivo methods can also be used in drug discovery Protein kinases and phosphatases have particularly been recognized as one of the more important general mechanism of cellular regulation. Protein phosphorylation commonly occurs on three major amino acids, tyrosine, serine or threonine. Changes in the phosphorylation state of these amino acids within proteins can regulate many aspects of cellular metabolism, regulation, grown and differentiation. Changes in the phosphorylation state of proteins, mediated through phosphorylation by kinases, or dephosphoryation by phosphatases, is a common mechanism through which cell surface signaling pathways transmit and integrate information into the nucleus. Given their key role in cellular regulation, it is not surprising that defects in protein kinases and phosphatases have been implicated in many disease states and conditions. For example, the over-expression of cellular tyrosine kinases such as the EGF or PDGF receptors, or the mutation of tyrosine kinases to produce constitutively active forms (oncogenes) occurs in many cancer cells (Durker et al. Nature Medicine 2:561–556 (1996)). Protein tyrosine kinases are also implicated in inflammatory signals, and defective Thr/Ser kinase genes have been demonstrated to be implicated in several diseases such as myotonic dystrophy, cancer and Alzheimer's disease (Sanpei et al., Biochem. Biophys. Res. Commun. 212:341–346 (1995); Sperger et al., Neurosci. Lett. 197:149–153 (1995); Grammas et al., Neurobiology of Aging, 16:563–569 (1995); Govani et al., Ann. N.Y. Acad. Sci. 777:332–337 (1996)).

The involvement of proteases, protein kinases, protein phosphatases, and other classes of enzymes in disease states makes them attractive targets for the therapeutic intervention of drugs. In fact, many clinically useful drugs act on protein kinases or phosphatases. Examples include cyclosporin A, a potent immunosuppresent that binds to cyclophilin. This complex binds to the $Ca^{++}$/calmodulin-dependent protein phosphatase type 2B (calcineurin), inhibiting its activity, and hence the activation of T cells. Inhibitors of protein kinase C are in clinical trials as therapeutic agents for the treatment of cancer (Clin. Cancer Res. 1:113–122 (1995)) as are inhibitors of cyclin dependent kinase (J. Mol. Med. 73:509–514 (1995)).

The number of known enzymes, such as kinases and phosphatases, are growing rapidly as the influence of genomic programs to identify the molecular basis for diseases have increased in size and scope. These studies are likely to implicate many more genes that encode enzymes that are involved in the development and propagation of diseases in the future, thereby making them attractive targets for drug discovery. However, current methods of measuring enzyme activity, such as protein phosphorylation and dephosphorylation, have many disadvantages which prevents or limits the ability to rapidly screen for drugs using miniaturized automated formats of many thousands of compounds. In the case of phosphatases and kinases, this is because current methods rely on the incorporation and measurement of $^{32}P$ into the protein substrates of interest. In whole cells this necessitates the use of high levels of radioactivity to efficiently label the cellular ATP pool and to ensure that the target protein is efficiently labeled with radioactivity. After incubation with test drugs, the cells must be lysed and the protein of interest purified to determine its relative degree of phosphorylation. This method requires high numbers of cell, long preincubation times, careful manipulation, and washing steps to avoid artifactal phosphorylation or dephosphorylation. Furthermore, this approach requires purification of the target protein, and final radioactive incorporation into target proteins is usually very low, giving the assay poor sensitivity. Alternative assay methods, such as those based on phosphorylation-specific antibodies using ELISA-type approaches, involve the difficulty of producing antibodies that distinguish between phosphorylated and non-phosphorylated proteins, and the requirement for cell lysis, multiple incubations, and washing stages which are time consuming, complex to automate, and potentially susceptible to artifacts.

Fluorescent molecules are attractive as reporter molecules in many assay systems because of their high sensitivity and ease of quantification. Recently, fluorescent proteins have been the focus of much attention because they can be produced in vivo by biological systems and can be used to trace and monitor intracellular event without the need to be introduced into the cell through microinjection or permeabilization. The green fluorescent protein of Aequorea victoria is particularly interesting as a fluorescent indicator protein. A cDNA for the protein has been cloned (Prasher et al., Gene 111:229–233 (1992)). Not only can the primary amino acid sequence of the protein be expressed from the cDNA, but the expressed protein can fluoresce in cells in vivo.

Fluorescent proteins have been used as markers of gene expression, tracers of cell lineage, and as fusion tags to monitor protein localization within living cells (Rizzuto et al., Current Biol. 6:183–188 (1996)); Cubitt et al., TIBS 20:448–455 (1995); U.S. Pat. No. 5,625,048 to Tsien et al, issued Apr. 29, 1997). Furthermore, mutant versions of green fluorescent protein have been identified that exhibit altered fluorescence characteristics, including altered excitation and emission maxima, as well as excitation and emission spectra of different shapes. (Heim, Proc. Natl. Acad. Sci. USA 91:12501–12504 (1994); Heim et al., Nature 373:663–665 (1995); U.S. Pat. No. 5,625,048, Tsien et al., issued Apr. 29, 1997; WO 97/28261 to Tsien et al, published Aug. 7, 1997; PCT/US 97/12400 to Tsien, filed Jul. 16, 1997; and PCT/US 97/14593 by Tsien, filed Aug. 15, 1997). These proteins add variety and utility to the arsenal of biologically based fluorescent indicators.

There is thus a need for assays for enzymes, such as those involved in protein phosphorylation, that are sensitive, simple to use, useful in living cells, and adaptable to high throughput screening methods. Preferably, such assays would not utilize radioactive materials so that the assays would be safe and not generate hazardous wastes. The present invention addresses these needs, and provides additional benefits as well.

BRIEF DESCRIPTION OF THE FIGURES

FIG. 1A and FIG. 1B depicts the nucleotide sequence (SEQ ID NO:1) and deduced amino acid sequence (SEQ ID NO:2) of wild-type *Aequorea* green fluorescent protein.

FIG. 2A and FIG. 2B depicts a list of the positions and amino acid changes made for phosphorylation mutants made more than fifteen amino acids in the primary sequence form the N-terminus, as compared to FIG. 1A and FIG. 1B. Amino acids underlined represent the phosphorylation motif, amino acids in brackets represent wild type sequence at those positions.

SUMMARY

Figure 3:
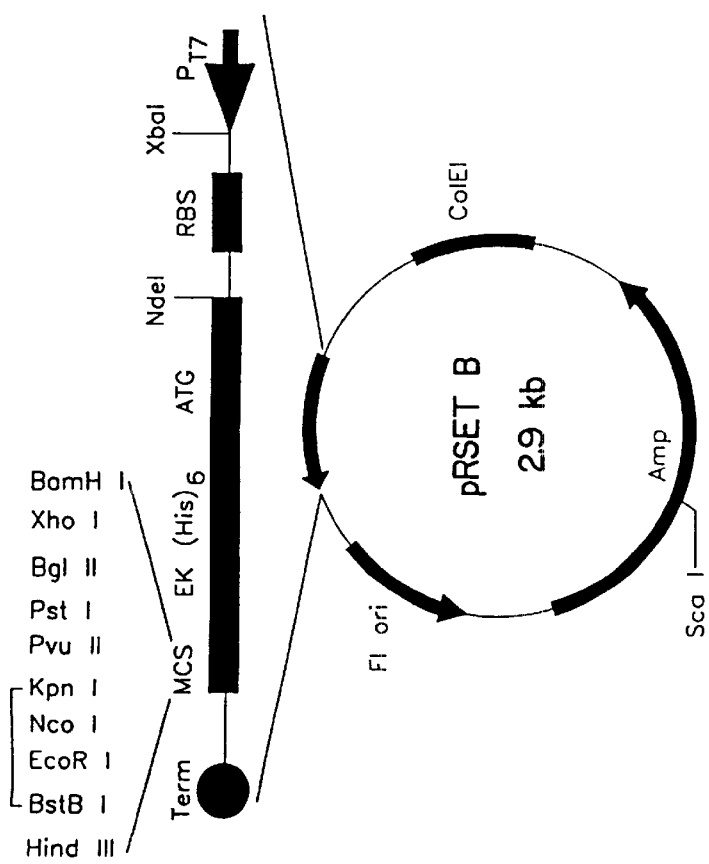
FIG. 3 depicts the bacterial expression plasmid pRSET (Invitrogen) containing a region encoding GFP that is fused in frame with nucleotides encoding an N-terminal polyhistidine tag.

The present invention recognizes that fluorescent compounds, such as fluorescent proteins, can exist in at least two states and that the fluorescent properties of these two states can be different, preferably after exposure of the fluorescent compound to quenching conditions. Particularly, the stability of the fluorescence in one state can be different from the stability of the fluorescence in the second state, which can be detected by their susceptibility to quenching. The first and second states of the fluorescent compound can be caused by the action of a chemical or enzyme. Thus, the present invention recognizes that such fluorescent compounds can be used to detect various chemical or enzymatic activities in a sample. The present invention recognizes that fluorescent compounds can be fluorescent proteins that can be expressed in cells. Thus, the fluorescent proteins can be used as in vivo monitors of enzymatic activity (intracellular or extracellular) and can be used to screen compounds for drugs that modulate (i.e., increase or decrease the activity) an enzymatic activity. The present invention also provides nucleic acid molecules that encode fluorescent proteins that exhibit quenching.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein, and the laboratory procedures in cell culture, molecular genetics, and nucleic acid chemistry and hybridization described below, are those well known and commonly employed in the art. Standard techniques are used for recombinant nucleic acid methods, polynucleotide synthesis, and microbial culture and transformation (e.g., electroporation, and lipofection). Generally, enzymatic reactions and purification steps are performed according to the manufacturer's specifications when kits or purchased reagents or materials are used. The techniques and procedures are generally performed according to conventional methods in the art and various general references (see generally, Sambrook et al., Molecular Cloning: A Laboratory Manual, 2d ed. (1989) Cold Spring Harbor Laboratory Press, Cold Spring Harbor, N.Y.) which are provided throughout this document. The nomenclature and laboratory procedures used herein are those well known and commonly employed in the art. As used throughout the disclosure, the following terms, unless otherwise indicated, shall be understood to have the following meanings.

"Quenching" or "quenching conditions," as used herein, means conditions that can cause a change in at least one fluorescent property of a fluorescent compound in a first state as compared to a second state. Quenching can be used, for example, to detect or measure the presence or concentration of the fluorescent compound in the first state or second state. Quenching conditions can include at least one quenching agent.

A first state or a second state of a fluorescent compound means that the fluorescent compound exists in at lest two states, wherein the different states have different fluorescent properties that can be detected by quenching. The first state can differ from the second state, for example, by the covalent attachment of moieties to the fluorescent compound, the binding or association of moieties to the fluorescent compound, the cleavage or disruption of covalent or non-covalent bonds or interactions on or within the fluorescent compound, the binding or association of the fluorescent compound to other moieties or itself, or a change in the conformation of the fluorescent compound as a result of the presence of an activity.

"Quenching agent," as used herein, can be any chemical, compound or biological molecule that can cause quenching of a fluorescent compound, either alone or in combination with other agents or factors.

A "fluorescent compound," as used herein, can be any fluorescent chemical or compound that can exhibit at least one different fluorescent property in a first state and a second state under quenching conditions. For example, fluorescent compounds can be small aromatic compounds such as fluorescein or rhodamine, or a weakly or non-fluorescent compound such as, for example carbohydrates, lipids, proteins, peptides, polypeptides, nucleic acids that has been labeled with a highly fluorescent compound or combinations thereof. For example, a fluorescent compound can be a fluorescent protein moiety. A fluorescent compound, such as those comprising a fluorescent protein moiety, can be soluble, membrane bound, or membrane associated. Membrane bound versions of soluble fluorescent protein moieties can be made by adding, for example, hydrophobic regions such as signal sequences or hydrophobic moieties as they are known in the art using established methods. Likewise, membrane associated versions of soluble fluorescent protein moieties can be made by adding, for example, membrane association motifs, such as poly-Lys, to such fluorescent protein moieties using established methods.

A "fluorescent protein moiety" means any protein or fragment thereof capable of fluorescence when excited with appropriate electromagnetic radiation. This includes fluorescent proteins whose amino acid sequences are either naturally occurring or engineered (i.e., analogs) and proteins that have been modified to be fluorescent, such as by the addition of a fluorescence compound, such as fluorescein, rhodamine, Cy3-5, Cy-PE, lucifer yellow, C6-NBD, Dio-Cn (3), FITC, Biodipy-FL, eosin, propidium iodide, tetramethyl rhodamine B, Dil-Cn-(3), Lissamine Rhodamine B, Texas Red, Allophycocyanin, Dil-Cy-5, and squaranes by methods known in the art. For fluorescent compounds, see Molecular Probes Catalogue (1998), U.S. Pat. No. 5,631,169, issued May 20, 1997, U.S. Pat. No. 5,145,774, issued Sep. 8, 1992, Many cnidarians use green fluorescent proteins ("GFPs") as energy-transfer acceptors in bioluminescence. A "green fluorescent protein," as used herein, is a protein that fluoresces green light. Similarly, "blue fluorescent proteins" fluoresce blue light and "red fluorescent proteins" fluoresce red light. GFPs have been isolated from the Pacific Northwest jellyfish, *Aequorea victoria*, the sea pansy, *Renilla reniformis*, and *Phialidium gregarium* (W.W. Ward et al., Photochem. Photoobiol, 35:803–808 (1982); Levine et al, Comp. Biochem. Physiol., 72B:77–85 (1982); and Roth, Purification and Protease Susceptibility of the Green-Fluorescent Protein of *Aequorea Aequorea* With a Note on Halistaura, Dissertation, Rutgers, The State University of New Jersey, New Brunswick, N.J. (1985)). GFPs have also been engineered to be blue fluorescent proteins and yellow fluorescent proteins (U.S. Pat. No. 5,625,048 to Tsien et al., issued Apr. 29, 1997; WO 97/28261 to Tsien et al., filed Jul. 16, 1997; PCT/US 97/14593 to Tsien et al., filed Aug. 15, 1997; WO 97/28261 to Tsien, published Aug. 7, 1997; and WO 96/23810 to Tsien et al., published Aug. 18, 1996).

An "Aequorea-related fluorescent protein" means any protein that has any contiguous sequence of 150 amino acids that has at least 85% sequence identity with an amino acid sequence, either contiguous or non-contiguous, from the 238 amino acid wild-type Aequorea green fluorescent protein of SEQ ID NO:2. More preferably, a fluorescent protein is an Aequorea-related fluorescent protein if any contiguous sequence of 200 amino acids of the protein has at least 95% sequence identity with an amino acid sequence, either contiguous or non-contiguous, from the wild type A equorea green fluorescent protein of SEQ ID NO:2. Similarly, the protein can be related to Renilla or Phialidium wild-type fluorescent proteins using the same standards.

A variety of Aequorea-related fluorescent proteins have been engineered by modifying the amino acid sequence of a naturally occurring GFP from *Aequorea victoria* (D.C. Prasher et al, Gene, 111:229–233 (1992); Heim et al. Proc. Natl. Acad. Sci. USA 91:12501–12504 (1994); U.S. Pat. No. 5,625,048, issued Apr. 29, 1997 to Tsien et al.; WO 96/23810 to Tsien, published Aug. 8, 1996; and PCT application PCT/US97/14593 to Tsien et al, filed Aug. 15, 1997) and have useful excitation and emission spectra.

A "substrate site for an activity" means a locus that is a substrate for an activity, such as an enzymatic activity. The locus can be any structure, such as an amino acid, chemical group or ionic or covalent bond. Such substrate site for an activity can be part of a substrate recognition motif that is recognized by an activity. For example, the site of phosphorylation within a protein is the actual amino acid modified by a phosphatase or kinase, and the site of phosphorylation can be within a phosphorylation recognition motif. A fluorescent compound or fluorescent protein moiety can have at least one substrate recognition motif, which can have at least one substrate site for an activity. Substrate recognition motifs that are recognized by enzymatic activities are known in the art, such as for proteases, kinases, phosphatases, glycosylases, or transferases (such as farnsyl transferases), or any other type of enzyme.

A "substrate recognition motif for an activity" can be any structure or sequence that is recognized by an enzyme that directs or helps in the enzymatic modification of the substrate by the enzyme. The substrate recognition motif for an activity can be within, close to, or part of the structure, such as amino acid residue or residues, that are modified by the activity, such as an enzyme activity, (such as the substrate site for an activity). For example, the sequence surrounding a protein kinase A phosphorylation site plays a significant role in controlling how efficiently the site is modified. Also, protein-protein interaction domains and protein localization domains can control the efficiency of enzymatic modifications of a substrate, such as a protein substrate, and are particularly important within cells (see, Pawson et al., Science 278:2075–2080 (1997). These protein-protein interaction domains and protein localization domains can be distal from the substrate recognition motif and play a role in substrate recognition.

A "fluorescent protein substrate" is a substrate for an activity, such as an enzymatic activity, that comprises a fluorescent compound that comprises a fluorescent protein moiety and at least one substrate site for an activity.

As used herein the term "phosphorylation recognition motif for a protein kinase" refers to an amino acid sequence that is recognized by a protein kinase for the attachment of a phosphate moiety. The phosphorylation recognition motif for a protein kinase can be a site recognized by, for example, protein kinase A, a cGMP-dependent protein kinase, protein kinase C, $Ca^{2+}$/calmodulin-depending protein kinase I, $Ca^{2+}$/calmodulin-dependent protein kinase II or MAP kinase activated protein kinase type 1, and isoforms or allelic variants thereof As used herein, "fluorescent property" refers to the molar extinction coefficient at an appropriate excitation wavelength, the fluorescent quantum efficiency, the shape of the excitation spectrum or emission spectrum, the excitation wavelength maximum or emission wavelength maximum, the ratio of excitation amplitudes at two different wavelengths, the ratio of emission amplitudes at two different wavelengths, the excited state lifetime, the fluorescent anisotropy or any other measurable property of a fluorescent compound. A measurable difference in any one of these properties in response to a quenching agent or under quenching conditions between a first state and a second state of a fluorescent compound suffices for the utility of the fluorescent compounds of the invention.

A difference in a fluorescent property of a fluorescent compound can be measured by determining the amount of any quantitative fluorescent property, e.g., the amount of fluorescence at a particular wavelength, or the integral of fluorescence of the emission spectrum. Determining ratios of excitation amplitude or emission amplitude at two different wavelengths ("excitation amplitude ratioing" and "emission amplitude ratioing," respectively) are particularly advantageous because the ratioing process provides an internal reference an cancels out variations in the absolute brightness of the excitation source, the sensitivity of the detector, and light scattering or quenching by the sample. Furthermore, if a change in a fluorescent compound from a first state to a second state changes the fluorescent compound's ratio of excitation or emission amplitudes at two different wavelengths, then such ratios measure the extent of the first state and second state independent of the absolute quantity of the fluorescent compound.

Introduction

The present invention recognizes that fluorescent compounds, such as fluorescent proteins, can exist in at least two states and that the fluorescent properties of these two states can be different, preferably under quenching conditions, and reflect different biochemical or chemical characteristics of the fluorescent compounds. Particularly, the stability of the fluorescence in one state can be different from the stability of the fluorescence in the second state, which can be detected by a sensitivity to quenching. The conversion of a first state to a second state of the fluorescent compound can be caused by the action of a chemical or enzyme, such as a protease, kinase, phosphatase, glycosylase, transferase such as protein prenyl transferase, or any other enzyme that can modify the fluorescent compound. Binding of moieties or hybridization (in the case of nucleic acids such as DNA or RNA) can also alter the fluorescence properties of a fluorescent compound after quenching. Thus, the present invention recognizes that such fluorescent compounds can be used to detect various enzymatic activities in a sample, such as in a cell, a cell culture, a cell extract, conditioned medium, or in an array. Such hybridization or binding can occur and be detected in high-density arrays or on gene chips such as they are known in the art (See, Johnson, Curr. Biol. 8:R171–4 (1998); Livache et al., Anal. Biochem. 255:188–194 (1998)). The present invention recognizes that fluorescent compounds can be fluorescent proteins and that these fluorescent proteins can be expressed in cells. Thus, the fluorescent proteins can be used as in vivo monitors of intracellular enzymatic activity and used to screen compounds for drugs that modulate an enzymatic activity. The present invention also provides nucleic acid molecules that encode fluorescent proteins that exhibit quenching.

As a non-limiting introduction to the breath of the invention, the invention includes several general and useful aspects, including:

1) A fluorescent compound for detecting an activity, comprising a fluorescent protein and a substrate recognition motif for an activity, wherein said fluorescent compound exhibits quenching, 2) A nucleic acid molecule coding for the expression of the fluorescent compound in 1), 3) A cell comprising the nucleic acid molecule of 2) or fluorescent compound of 1), 4) A method for determining whether a sample contains an activity, comprising contacting a sample with a fluorescent compound of 1), exciting said fluorescent compound, and measuring the amount of emission from said fluorescent compound under quenching conditions, and 5) A method for determining whether a cell exhibits an activity comprising exciting a transfected host cell comprising a recombinant nucleic acid molecule of 2) or fluorescent compound of 1), and measuring the emission from the fluorescent compound under quenching conditions.

Fluorescent Compounds for Detecting an Activity

The present invention provides fluorescent compounds for detecting an activity, comprising: a fluorescent protein and at least one substrate site for an activity, wherein said fluorescent compound can exist in at lease two states that exhibit quenching.

The sensitivity of the fluorescent compound to quenching is influenced by a modification of the fluorescent compound from a first state to a second state by an activity, such as an enzymatic activity. Such modification of the fluorescent compound can stabilize or destabilize the fluorescent compound by, for example, changing the conformation of the fluorescent compound, the addition of a moiety to the fluorescent compound, or the removal of a moiety from the fluorescent compound. Exposure of the fluorescent compound to chemicals or enzymes can cause such modifications.

For example, a ligand binding to a fluorescent compound can alter a fluorescent property of the fluorescent compound, making the fluorescent compound more or less sensitive to quenching. Likewise, the association of moieties with a fluorescent compound (by, for example, chemical or enzymatic reaction) or the aggregation of fluorescent compounds, or hybridization of nucleic acids, can alter at least one fluorescent property of a fluorescent compound that can be detected by quenching. Furthermore, moieties can be added to a fluorescent compound by covalent modification that can result in an altered fluorescent property of the fluorescent compound that can be detected by quenching. Likewise, covalent bonds can be cleaved within the structure of the fluorescent compound that can result in an altered fluorescent property of the fluorescent compound that can be detected after quenching.

Covalent bonds can be made or broken by well-known chemical or enzymatic reactions. For example, peptide bonds can be hydrolyzed by acidic conditions or by proteases. Also, phosphate groups can be added to a fluorescent compound by kinases, and removed by phosphatases. Other enzymatic reactions, such as lipases, the addition or loss of lipid moieties such as farnsyl, geranylgeranyl or phosphatidyl inositol groups, and the like can be used to modify fluorescent compounds, which can in turn alter a fluorescent property of the fluorescent compound that can be measured by quenching.

A change in the number or distribution of disulfide bonds by an alteration in the redox state thereof can also alter a fluorescent property of a fluorescent compound. For example, reducing agents, such as beta-mercaptoethanol, can alter the oxidation state of disulfide bonds within a fluorescent compound having such structures. The change in the structure of the fluorescent compound caused by such treatment can cause a change in a fluorescent property of the fluorescent compound that can be detected after quenching.

When an activity can modify a fluorescent compound, the fluorescent compound can comprise a naturally occurring substrate recognition motif (for example, endogenous to the fluorescent compound) for such enzymatic reactions, or such substrate recognition motifs can be added or engineered into the fluorescent compound (for example exogenous to the fluorescent compound). For example, a fluorescent compound that is a protein can be engineered to comprise a substrate recognition motif for a protease, protein phosphatase, protein kinase, protein prenyltransferase, glycosylase, or any other enzyme using methods known in the art. For example, genetic engineering, chemical modification techniques, or enzyme reactions can be used to add such substrate recognition motifs to the amino- or carboxy-terminus of a fluorescent compound. Alternatively, these techniques can be used to insert such substrate recognition motifs within the structure of the fluorescent compound.

A change in the tertiary structure of a fluorescent compound by the addition or removal of a moiety by chemical or enzymatic activity can also cause a change in a fluorescent property of a fluorescent compound after quenching. For example, phosphorylation of a fluorescent compound can lead to a change in its tertiary structure through the creation of new or stronger interactions between amino acid residues, which can result in stabilized fluorescence that can result in increased resistance to quenching. Such a change in sensitivity to quenching can subsequently be used to measure the amount of fluorescent compound that has been phosporylated, and hence the activity of the kinase can be detected and/or measured. Such moieties can also destabilize the tertiary structure of a fluorescent protein, which can result in destabilized fluorescence under quenching conditions. Furthermore, enzymatic activities such as proteases can alter the tertiary structure of a fluorescent protein, which can also result in destabilized fluorescence under quenching conditions. Furthermore, the presence of an electrochemical, chemical or electrical gradient or potential can also change a fluorescent property of a fluorescent compound that can be detected through quenching.

Quenching agents can be used to detect the stabilization, destabilization, or protection of a fluorescent property of a fluorescent compound arising from an activity. For example, fluorescent compounds such as fluorescent proteins can be stabilized or destabilized by acidic conditions, basic conditions, surfactants, organic solvents, chaotropic salts or agents, anti-chaotropic salts or agents, reducing conditions or agents, oxidizing conditions or agents, paramagnetic ions, enzymes, collisional quenchers, temperature or any combination thereof.

Fluorescent compounds, such as fluorescent proteins, can be made using methods known in the art. For example, fluorescent proteins can be made by expressing nucleic acids that encode fluorescent proteins, such as wild-type or mutant Aequorea green fluorescent protein, or other fluorescent proteins such as those from Renilla, in an appropriate cellular host (WO 96/2381 to Tsien et al., published Aug. 18, 1996). Alternatively, proteins that are otherwise not fluorescent can be made fluorescent by covalently linking or binding a fluorophore, such as fluorescein, to the protein using methods known in the art (U.S. Pat. No. 5,605,809 to Kumoriya et al., issued Feb. 25, 1997).

Fluorescent compounds, such as fluorescent proteins, can have structures that allow them to be altered from a first state to a second state by, for example, binding of a ligand, post translational modifications such as phosphorylation, dephosphorylation, proteolysis, or glycosylation at specific sites. Compounds can be modified to include such specific sites using methods known in the art. For example, fluorescent proteins, such as Aequorea green fluorescent protein, can be engineered to have non-naturally occurring substrate recognition motifs, such as known phosphorylation or protease motifs and sites. The phosphorylation or proteolytic status of the fluorescent compound can alter the stability of the compound such that the phosphorylated, unphosphorylated, or proteolytic states of the fluorescent compound can be detected or measured using quenching.

Optimal alignment of sequences for aligning a comparison window may be conducted by the local homology algorithm of Smith and Waterman (Adv. Appl. Math, 2:482 (1981)) by the homology alignment algorithm of Needleman and Wunsch (J. Mol. Biol. 48:443 (1970)) by the search for similarity method of Pearson and Lipman (Proc. Natl. Acad. Sci. USA 85:2444 (1988)) by computerized implementations of algorithms GAP, BESTFIT, FASTA, and TFASTA in the Wisconsin Genetics Software Package (Release 7.0, Genetics Computer Group, Madison, Wis.) or by inspection. The best alignment, (i.e. resulting in the highest percentage of homology over the comparison window, i.e., 150 or 200 amino acids) generated by the various methods is preferably selected. The percentage of sequence identity is calculated by comparing two optimally aligned sequences over the window of comparison, determining the number of positions at which the identical amino acid occurs in both sequences to yield the number of matched positions, dividing the number of matched positions by the total number of positions in the window of comparison (i.e. the window size), and multiplying the results by 100 to yield the percentage of sequence identity.

Aequorea-related fluorescent proteins include, for example, and without limitation, wild-type (native) Aequorea victoria GFP (Prasher, Gene 111:229–233 (1992), whose nucleotide sequence (SEQ ID NO:1) and deduced amino acid sequence (SEQ ID NO:2), allelic variants or other variants of this sequence (for example, Q80R, which has the glutimine residue at position 80 substituted with arginine (Chalfie et al, Science, 263:802–805 (1994)), those Aequorea-related engineered versions described in TABLE I, variants that include one or more folding mutants and fragments of these proteins that are fluorescent, such as Aequorea green fluorescent protein form which the two amino-terminal amino acids have been removed from the amino- or carboxy-terminus. Several of these contain different aromatic amino acids within the central chromophore and fluoresce at a distinctly shorter wavelength than wild type species. For example, mutants P4 and P4-3 contain, in addition to other mutations, the substitution Y66H. Mutants W2 and W7 contain, in addition to other mutations, Y66W. Other mutations, provided as non-limiting examples are listed in TABLE I. The following six groups each contain amino acids that are conserved substitutions for one another.

1) Alanine (A), Serine (S), Threonine (T),
2) Aspartic Acid (D), Glutamic Acid (E),
3) Asparagine (N), Glutamine (Q),
4) Arginine (R), Lysine
5) Isoleucine (I), Leucine (L), Methionine (M), Valine (V), and
6) Phenylalanine (F), Tyrosine (Y), Tryptophan (W).

Other mutations are set forth in U. S. Pat. No. 5,625,048 to Tsien et al., issued Apr. 29, 1997; WO 96/23810 to Tsien et al., published Aug. 18, 1996; PCT/US 97/12410 to Tsien et al., filed Jul. 16, 1997; PCT/US 97/14593 to Tsien et al., filed Aug. 15, 1997; and PCT/US 96/04059 to Tsien et al., filed Mar. 20, 1996.

TABLE I

Fluorescent mutants of Aequorea green fluorescent protein

| Clone | Mutation(s) | Excitation Max (nm) | Emission Max (nm) | Extinction Coefficient (M-1 cm-1) | Quantum Yield |
|---|---|---|---|---|---|
| Wild type | None | 395 (475) | 508 | 21,000 (7,150) | 0.77 |
| P4 | Y66H | 383 | 447 | 13,500 | 0.21 |
| P4-3 | Y66H Y145F | 381 | 445 | 14,000 | 0.38 |
| W7 | Y66W N146I M153T V163A N212K | 433 (453) | 475 (501) | 18,000 (17,000) | 0.67 |
| W2 | Y66W I123V Y145H H148R M153T V163A N212K | 432 (453) | 480 | 10,000 (9,600) | 0.72 |
| S65T | S65T | 489 | 511 | 39,200 | 0.68 |
| P4-1 | S65T M153A K238E | 504 (396) | 514 | 14,500 (8,600) | 0.53 |
| S65A | S65A | 471 | 504 | | |
| S65C | S65C | 497 | 507 | | |
| S65L | S65L | 484 | 510 | | |
| Y66F | Y66F | 360 | 442 | | |
| S65T | S65T | 489 | 511 | 39,200 | 0.68 |
| Y66H | Y66H | 382 | 448 | | |
| Y66W | Y66W | 458 | 480 | | |
| K4 | SEQ ID NO:.49 -2M -1G M1R S2R K3R G4A E5S E6I L7I S65A N149K V163A I167T | 471 | 505 | | |
| K5 | K4 + K79N | 471 | 505 | | |
| K6 | K4 + E90N | 471 | 505 | | |
| K7 | K4 + E90K | 471 | 505 | | |
| K8 | K4 + K79R E90N | 471 | 505 | | |
| K9 | K4 + K79R E90K | 471 | 505 | | |
| K10 | K4 + K79H E90N | 471 | 505 | | |
| K11 | K4 + K79H E90K | 471 | 505 | | |
| K12 | K4 + K79H | 471 | 505 | | |
| K13 | K4 + K79E E90N | 471 | 505 | | |
| K14 | K4 + K79E E90K | 471 | 505 | | |
| K15 | K4 + K79E | 471 | 505 | | |
| K16 | K4 + K79Q | 471 | 505 | | |
| K4 + E90A | K4 + E90A | 471 | 505 | | |
| K4 + E90L | K4 + E90L | 471 | 505 | | |
| K4 + E90V | K4 + E90V | 471 | 505 | | |
| K4 + E90T | K4 + E90T | 471 | 505 | | |
| K4 + E90S | K4 + E90S | 471 | 505 | | |
| K4 + E90I | K4 + E90I | 471 | 505 | | |

TABLE I-continued

Fluorescent mutants of Aequorea green fluorescent protein

| Clone | Mutation(s) | Excitation Max (nm) | Emission Max (nm) | Extinction Coefficient (M-1 cm-1) | Quantum Yield |
|---|---|---|---|---|---|
| K4 + K79R | K4 + K79R | 471 | 505 | | |
| I167T T203I | I167T T203I | 471 | 502 | | |
| H9 | S202F T203I | 398 | 511 | | |
| P9 | I167V | 471 (396) | 502 (507) | | |
| P11 | I167T | 471 (396) | 502 (507) | | |
| 10C | S65G V68L S72A T203Y | 513 | 527 | | |
| W1B | F64L S65T Y66W N146I M153T V163A N212K | 432 (453) | 476 (503) | | |
| Emerald | S65T S72A N149K M153T I167T | 487 | 508 | | |
| Topaz | S65G S72A K79R T203Y | 514 | 528 | | |
| P4-3E | Y66H Y145F F64L V163A | 382 | 446 | | |
| Sapphire | S72A Y145F T203I | 395 | 571 | | |

Additional mutations in A equorea-related fluorescent protein, referred to as "folding mutations," improve the ability of GFP to fold at higher temperatures, and to be more fluorescent when expressed in mammalian cells, but can have little effect on the peak wavelengths of excitation and emission. It should be noted that these folding mutants can be combined with mutations that influence the spectral properties of GFP to produce proteins with altered spectral and folding properties. Folding mutations include the following mutations: T44A, F64L, V68L, S72A, F99S, Y145F, N146I, S147P, M153T or A, V163A, I167T, S175G, S205T and N212K.

This invention contemplates the use of other fluorescent proteins in fluorescent protein substrates. The cloning and expression of yellow fluorescent protein from *Vibrio fisheri* strain YU-1 has been described by Baldwin et al. (Biochemistry 29:5509–5515 (1990)). This protein requires flavins as fluorescent cofactors. The cloning of Peridinin chlorophill a binding protein from the dinoflagellate Symbiodinium sp., was described by Morris et al, (Plant Molecular Biology 24:673–677 (1994)). One useful aspect of this protein is that is fluoresces red. The cloning of the phycobiliprotiens from marine cyanobacteria such as Synechoccus, e.g., phycoerythrin and phycocyanin, is described in Wilbands et al., (J. Biol. Chem. 268:1226–1235 (1993). These proteins sequence phycobilins as fluorescent co-factors, whose insertion into the proteins involves auxiliary enzymes. These protein fluoresce at yellow to red wavelengths.

It has been found that fluorescent proteins can be genetically fused to other proteins and used as markers to identify the location and amount of the target protein produced. Accordingly, this invention provides fusion proteins comprising a fluorescent protein moiety and additional amino acid sequences such as amino acid sequences encoding a protein or polypeptide or peptide of interest. Such additional amino acid sequences can be, for example, up to about 15, up to about 150 or up to about 1,000 amino acids long and comprise a substrate site for an activity, such as an enzymatic activity. The fusion proteins possess the ability to fluorescence when excited by electromagnetic radiation. In one embodiment, the fusion protein comprises a polyhistidine tag to aid in purification of the protein or a poly-Lys portion to aid in membrane association of the fluorescent compound.

Fluorescent protein substrates for a protein kinase are the subset of fluorescent proteins as defined above whose amino acid sequence includes a phophorylation recognition motif and site. Fluorescent protein substrates can be made by modifying the amino acid sequence of an existing fluorescent protein to include a phosphorylation recognition motif and site for a protein kinase.

A consensus phosphorylation recognition motif for protein kinase A is RRXSZ (SEQ ID NO:3) or RRXTZ (SEQ ID NO:4), wherein X is any amino acid and Z is a hydrophobic amino acid, preferably valine, leucine or isoleucine. Many variations in the above sequence are allowed, but generally exhibit poorer kinetics. For example lysine (K) can be substituted for the second arginine. Many consensus sequences for other protein kinases have been tabulated (e.g. by Kemp and Pearson, Trends Biochem. Sci. 15:342–346 (1990); Songyang et al., Current Biology 4:973–982 (1994); Nishikawa et al., J. Biol. Chem. 272952–960 (1997); and Songyang et al., Mol. Cell. Biol. 16:6486–6493 (1996)).

For example, a fluorescent protein substrate selective for phosphorylation by cGMP-dependent protein kinase can include the following consensus phosphorylation recognition motif sequence: BKISASEFDRPLR (SEQ ID NO:5), where B represents either lysine (K) or arginine (R), and the first S is the site of phosphorylation (Colbran et al, J. Biol. Chem. 267:9589–9594 (1992)). The residues DRPLR (SEQ ID NO:6) are less important than the phenylalanine (F) just preceding them for specific recognition by cGMP-dependent protein kinase in preference to cAMP-dependent protein kinase.

Either synthetic or naturally occurring phosphorylation recognition motifs can be used to create a protein kinase phosphorylation site. For example, peptides including the motif XRXXSXRX (SEQ ID NO:7), wherein X is any amino acid, are among the best synthetic substrates (Kemp and Pearson, supra) for protein kinase C. Alternatively, the Myristoylated Alanine-Rich Kinase C substrate ("MARCKS") is one of the best substrates for PKC and is an efficient real target for the kinase in vivo. The Examples set forth additional substrates for PKC. The phosphorylation recognition motif sequence around the phosphorylation site of MARCKS is KKKKRFSFK (SEQ ID NO:8) (Graffet al., J. Biol. Chem. 266:14390–14398 (1991)). Either of these two sequences can be incorporated into a fluorescent protein to make it a substrate for protein kinase C.

A protein substrate for Ca$^{2+}$/calmodulin-dependent protein kinase I is derived from the sequence of synapsin, a known optimal substrate for this kinase. The phosphorylation recognition motif around the phosphorylation site is LRRLSDSNF (SEQ ID NO:9) (Lee et al., Proc. Natl. Acad. Sci. USA 91:6413–6417 (1994)).

A protein substrate selective for Ca$^{2+}$/calmodulin-dependent protein kinase II is derived from the sequence of glycogen synthase, a known optimal substrate for this kinase. The recognition sequence around the phosphorylation site is KKLNRTLTVA (SEQ ID NO:10) (Stokoe et al. Biochem. J. 296:843–849 (1993)). A small change in this sequence to KKANRTLSVA (SEQ ID NO: 11) makes the latter specific for MAP kinase activated protein kinase type 1. Other preferred kinase recognition motifs and sites are provided in TABLE II below. One skilled in the art would realize that many proteins that do not contain such preferred phosphorylation motifs and sites can be phosphorylated if they conform to the consensus motif, but that the rates of phosphorylation can be less than for the preferred substrates.

TABLE II

| SEQ ID NO | Protein Kinase | Sequence |
| --- | --- | --- |
| SEQ ID NO. 50 | Cyclin B-CDC2 | HHHK<u>S</u>PRRR |
| SEQ ID NO. 51 | Cyclin A-CDK2 | HHHR<u>S</u>RPKR |
| SEQ ID NO. 52 | Protein Kinase A | RRRR<u>S</u>IIFI |
| SEQ ID NO. 53 | SLK 1 | RRFG<u>S</u>LRRL |
| SEQ ID NO. 54 | ERK 1 | TGPL<u>S</u>PGPF |
| SEQ ID NO. 55 | Protein Kinase Cα | RRRRRKG<u>S</u>FRRKA |

In one embodiment, the fluorescent protein substrate contains a phophorylation motif and site at or about one or more of the termini, in particular, the amino-terminus, of the fluorescent protein moiety. The site preferably is located in a position within five, ten, fifteen, or twenty amino acids of a position corresponding to the wild type amino-terminal amino acid of the fluorescent protein moiety. This includes sites engineered into the existing amino acid sequence of the fluorescent protein moiety and can also be produced by extending the amino terminus of the fluorescent protein moiety.

One may, for example, modify the existing sequence of wild type Aequorea GFP, or a variant thereof, to include a phosphorylation site within the first ten, twelve, fifteen, eighteen or twenty amino acids of the N-terminal met of wild-type Aequorea GFP (or its equivalent in a fusion protein). In one embodiment, the naturally occurring sequence is modified as follows:

Wild type: MSKGEELFTG residues    (1 to 10 of SEQ ID NO:2)

Substrate: MRRRR<u>S</u>IITG    (SEQ ID NO:12).

One may include modifying the naturally occurring sequence of Aequorea GFP by introducing a phosphorylation motif or site into an extended amino acid sequence of such a protein created by adding flanking sequences to the amino terminus, for example:

Wild type: MSKGEELFTG residues    (1 to 10 of SEQ ID NO:2)

Substrate MRRRR<u>S</u>IIIIFTG    (SEQ ID NO:13).

Fluorescent protein substrates having a phosphorylation site at or about a terminus of a fluorescent protein moiety offer the following advantages. First, it is often desirable to append additional amino acid residues onto the fluorescent protein moiety to create a specific phosphorylation consensus sequence. Such a sequence is less likely to disrupt the folding pattern of a fluorescent protein moiety when appended onto the terminus than when inserted into the interior of the protein sequence. Second, different phosphorylation motifs can be interchanged without significant disruption of GFP, thereby providing a general method of measuring different kinases. Third, the phosphorylation site is preferably exposed to the surface of the protein and, therefore, more accessible to protein kinases. Fourth, we have discovered that phosphorylation at sites close to the N-terminus of GFP can provide large changes in fluorescent properties if the site of phosphorylation is chosen such that the Ser or Thr residue that is phosphorylated occupies a position that was originally negative or positively charged in the wild-type protein. Specifically, replacement of Glu 5 or Glu 6 by a non-charged Ser or Thr residue can significantly disrupt the fluorescence, folding, or sensitivity of GFP to quenching. Phosphorylation of the serine or threonine can restore negative charge to this position and thereby increases the ability of GFP to fold correctly at higher temperatures, and hence can increase the fluorescence of GFP and resistance to quenching.

In another embodiment, the fluorescent protein substrate includes a phosphorylation site remote form a terminus, e.g., that is separated by more than about twenty amino acids from the terminus of the florescent protein moiety and within the fluorescent protein moiety. One embodiment of this form includes the Aequorea-related fluorescent protein substrate comprising the substitution H2 17S, creating a consensus protein kinase A phosphorylation motif and site. Additionally, phosphorylation recognition motifs comprising the following alterations based on the sequence of wild type Aequorea GFP exhibit fluorescent changes upon phosphorylation: 69RRFSA (SEQ ID NO:14) and 214KRDSM (SEQ ID NO:15) (which includes H217S).

The artisan should consider the following when selecting amino acids for substitution within the fluorescent protein moiety remote in primary amino acid sequence form the terminus. First, it is preferable to select amino acid sequences within the fluorescent protein moiety that resemble the sequence of the phosphorylation motif and site. In this way, fewer amino acid substitutions in the native protein are needed to introduce the phosphorylation motif and site into the fluorescent protein. For example, protein kinase A recognizes the sequence RRXSZ (SEQ ID NO:3) or RRXTZ (SEQ ID NO:4), wherein X is any amino acid and Z is a hydrophobic amino acid. Ser or Thr is the site of phosphorylation. It is preferable to introduce this sequence into the fluorescent protein moiety at sequences already containing Ser or Thr so that Ser or Thr are not substituted in the protein. More preferably, the phosphorylation recognition motif is created at locations having some existing homology to the sequence recognized by protein kinase A, e.g. having a proximal Arg or hydrophobic residues with the same spatial relationship as in the phosphorylation site.

Second, location on the surface of the fluorescent protein is preferred for phosphorylation sites. This is because surface locations are more likely to be accessible to protein kinaes than interior locations. Surface locations can be identified by computer modeling of the fluorescent protein structure or by reference to the crystal structure of Aequorea GFP. Also, charged amino acids or groups of charged amino acids in the fluorescent protein are more likely to lie on the surface than inside the fluorescent protein, because such amino acids are more likely to be exposed to water in the environment.

In cases where the phosphorylation site is either at a terminus, such as the N-terminus, or remote from a terminus, the amino acid context around the phosphorylation site can be optimized in order to maximize the change in fluorescence. Amino acid substitutions that change large bulky and/or hydrophobic amino acids to smaller and less hydrophobic replacements are generally helpful. Similarly, large charged amino acids can be replaced by smaller, less charged amino acids. For example:

a) Hydrophobic to less hydrophobic
  Phe to Leu
  Leu to Ala
b) Charged to charged but smaller
  Glu to Asp
  Arg to Lys
c) Charged to less charged
  Glu to Gln
  Asp to Asn
d) Charged to polar
  Glu to Thr
  Asp to Ser
e) Changed to non-polar
  Glu to Leu
  Asp to Ala These changes can be accomplished by direct means or using random iterative approaches where changes are made randomly and the best ones selected based upon their change in fluorescent properties after phosphorylation by an appropriate kinase.

Third, amino acids at distant locations from the actual site of phosphorylation can be varied to enhance fluorescence changes upon phosphorylation. These mutations can be created through site directed mutagenesis, or through random mutagenesis, for example by error-prone PCR, to identify mutations that enhance either absolute fluorescence or the change in fluorescence upon phosphorylation. The identification of mutants remote in primary sequence from a terminus, such as an N-terminus, identifies potentially interacting sequences that may provide additional areas in which further mutagenesis can be used to refine the change in fluorescence upon phosphorylation. For example, mutations around the amino terminus phosphorylation site may interact (either transiently during folding, or in a stable fashion) with amino acids at positions 171 and 172, and point mutations that significantly disrupt fluorescence of GFP by changing negative to positive charges near the amino terminus can be rescued by changing a positive to a negative charge at position 171.

In the phosphorylation mutant below the sequence is a), the wild type sequence b) is also listed below.

MSKRRDSLT (SEQ ID NO:16)  a)

MSKGEELFT (1 to 9 of SEQ ID NO:2)  b)

The phosphorylation mutant has only 7% of the fluorescence of the wild type protein. However, its fluorescence can be restored to 80% of the wild type by two amino acid changes, E171K and I172V, positions which are quite remote in linear sequence form the amino terminus.

Thus, changes in charge at E171K (negative to positive) can almost completely restore the fluorescence of the phosphorylation mutant, strongly suggesting that the original loss of fluorescence arose primarily through changes in charge caused by the point mutations. It is clear that the addition and loss of charge at positions around, and at the phosphorylation site, have a significant impact on fluorescence formation. The fact that charge alone can significantly affect the fluorescence properties of GFP is highly significant within the scope of the present application since phosphorylation involves the addition of two negative changes associated with the phosphate group on the serine residue.

In the above case the mutations restore fluorescence of the phosphorylation mutant without significantly increasing the magnitude of the change in fluorescence upon phosphorylation. Nevertheless, the identification of these positions in GFP provides a valuable tool to further enhance changes in fluorescence upon phosphorylation by creating random mutations at codons around positions 171, 172, and 173 to identify mutations that enhance changes in fluorescence upon phosphorylation. This can be achieved by co-expressing the kinase of interest with the fluorescent substrate of the present invention containing random mutations that may enhance the fluorescence changes upon phosphorylation.

A GFP-based phosphorylation sensor having a phosphorylation motif or site at or near the amino-terminus can be modified to establish a phosphorylation sensor having enhanced fluorescence, enhanced kinetics of phosphorylation, and enhanced changes in fluorescence upon quenching. Within the amino terminal sequence of GFP the first four amino acids are freely interchangeable. The next seven amino acids can be modified, preferably with conservative amino acid changes, to accommodate a phosphorylation recognition motif. To achieve high levels of fluorescence, it may be preferable to mutate addition sites in GFP to promote efficient folding. These methods are discussed in the Examples. In addition to enhancing fluorescence of such sensors, the kinetics of phosphorylation of these sensors can be enhanced. For example, the efficiency with which a phosphorylation site is modified by a kinase or phosphatase is dependent on the sequence and accessibility of the recognition motif. The accessibility of the phospohrylation motif can be improved my making changes in amino acids that disorder the local amino-terminal structure of GFP or reduce interactions between the amino-terminal region and the interior of the molecule, preferably by disrupting interactions between Lys3 and Glu90 and amino acids around these residues.

Preferable mutants can be identified using, for example, the following method. Nucleic acid molecules encoding such fluorescent compounds, such as kinase sensors, can be placed into an appropriate expression vector. The expression vector can also encode an activity, such as an activity specific for the fluorescent compound, such as a kinase. The expression vectors are transformed into host cells, such as bacteria or mammalian cells, such as human cells, and the individual bacterial colonies grown up. Each colony is derived from a single cell, and hence contains a single unique mutant fluorescent substrate grown up. The individual colonies may then be grown up and screened for fluorescence either by fluorescence activated cell sorting (FACS), or by observation under a microscope. Those that exhibit the greatest fluorescence can then be screened under conditions in which the gene encoding the activity, such as a kinase activity, is inactivated. Appropriate digests of the kinase gene can achieve this by restriction enzymes that specifically cut within the kinase but not GFP. Comparison of the brightness of the mutant first in the presence of kinase then in its absence indicates the relative effect of phosphorylation o the mutant GFP.

Fluorescent protein substrates for a protease can be made using the methods and strategies discussed above for fluorescent protein substrates for a protein kinase. The skilled artisan need merely incorporate a protease cleavage recognition site into the fluorescent compound rather than a substrate site for a protein kinase. Such protease cleavage recognition sites are known in the art, some of which are presented in TABLE III.

TABLE III

| Protease | Sequence |
|---|---|
| HIV-1 protease | SQNY-PIVQ (SEQ ID NO: 37) |
| | KARVL-AEMS (SEQ ID NO: 38) |
| Prohormone convertase | PSPREGKR-SY (SEQ ID NO: 39) |
| Interleukin-1b-converting enzyme | YVAD-G (SEQ ID NO.: 40) |
| Adenovirus endopeptidase | MFGG-AKKR (SEQ ID NO: 41) |
| Cytomegalovirus assemblin | GVVMA-SSRLA (SEQ ID NO: 42) |
| Leishmanolysin | LIAYI-LKKAT (SEQ ID NO: 43) |
| b-Secretase for amyloid precursor protein | VKM-DAEF (SEQ ID NO: 44) |
| Thrombin | FLAEGGGVR-GPRVVERH (SEQ ID NO: 45) |
| | DRVYIHPF-HL-VIH (SEQ ID NO. 46) |
| Renin and angiotensin-converting Enzyme | |
| Cathepsin D | KPALF-FRL (SEQ ID NO: 47) |
| Kininogenases including kallikrein | QPLGQTSLMK-RPPGFSPFR SVQVMKT QEGS (SEQ ID NO: 48) |

See, e.g., Matayoshi et al. (1990) Science 247:954, Dunn et al. (1994) Meth. Enzymol. 241:254, Seidah I& Chretien (1994) Meth. Enzymol. 244:175, Thornberry (1994) Meth. Enzymol. 244:615, Weber & Tihanyi (1994) Meth. Enzymol. 244:595, Smith et al.(1994) Meth. Enzymol. 244:412, Bouvier et al. (1995) Meth. Enzymol. 248:614, Hardyi et al. (1994) in *Amyloid Protein Precursor in Development, Aging, and Alzheimer's Disease,*

The methods discussed above can be used to confirm that a fluorescent compound comprising a protease cleavage motif and site exhibits at least one different fluorescent property in the cleaved and uncleaved state In addition to protein kinase substrates, protein phosphatase substrate, and protease substrates, the present invention encompasses substrates for protein prenyltransferases, glycosylases, any other enzyme recited in this application, any other known enzyme, or any enzyme later discovered. Fluorescent compounds that are substrates for these enzyme activities can be made using the methods described in the present application following the exemplary teachings set forth in the Examples. For example, different substrate recognition motifs and substrate sites for activities, such as enzyme activities, can be incorporated into GFP to make and confirm that compounds that can exhibit quenching in response to an activity. Furthermore, fluorescent compounds other than GFP that have at least one substrate recognition motif and site for activities can be made and confirmed to exhibit quenching in response to an activity by following the exemplary teachings set forth in the Examples.

Furthermore, the present invention encompasses substrate sites for an activity, such as an enzymatic activity, that exhibits at least one different fluorescent property in a first and second state after quenching that can be detected by fluorescent detection methods. Such activities include proteases, transferases, glycosylases, reductases, oxidases, or any other enzyme recited in this application, any other known enzyme, or any enzyme later discovered. Such substrates can be made using the exemplary teachings set forth in the Examples.

Nucleic Acid Molecules Coding for the Expression of a Fluorescent Compound

While certain florescent compounds can be prepared chemically, for example, by coupling a fluorescent moiety to the amino terminus of a protein moiety, it is preferable to produce fluorescent compounds comprising a peptide or protein recombinantly.

Recombinant production of a fluorescent compound involves expressing a nucleic acid molecule having sequences that encode a peptide or protein. As used herein, the term "nucleic acid molecule" includes both DNA and RNA molecules. It will be understood that when a nucleic acid molecule is said to have a DNA sequence, this also includes RNA molecules having the corresponding RNA sequence in which "U" replaces "T." The term "recombinant nucleic acid molecule" refers to a nucleic acid molecule which is not naturally occurring, and which comprises two nucleotide sequences that are not naturally joined together. Recombinant nucleic acid molecules are produced by artificial combination, e.g., genetic engineering techniques or chemical synthesis.

In one embodiment, the nucleic acid encodes a fusion protein in which a single polypeptide includes the fluorescent protein moiety within a longer polypeptide In another embodiment, the nucleic acid encodes the amino acid sequence that comprises a substrate site for an activity consisting essentially of a fluorescent protein moiety modified to include a substrate site for an activity. In either case, nucleic acids that encode fluorescent proteins are useful as starting materials.

Nucleic acids encoding a fluorescent protein moiety can be obtained by methods known in the art. For example, a nucleic acid encoding a GFP can be isolated by polymerase chain reaction of cDNA from A. Victoria using primers based on the DNA sequence of A. victoria green fluorescent protein (SEQ ID NO:2). PCR methods are described in, for example, U.S. Pat. No. 4,683,195; Mullis et al, cold Spring Harbor Symp. Quant. Biol. 51:263 (1987); and Erlich, PCR Technology, Stockton Press, NY (1989).

Mutant versions of fluorescent proteins can be made by site-specific mutagenesis of other nucleic acids encoding a fluorescent protein moiety or by random mutagenesis caused by increasing the error rate of PCR of the original polynucleotide with 0.1 mM $MnCl_2$ and unbalanced nucleotide concentrations (U.S. Pat. No. 5,625,048 to Tsien, issued Apr. 29, 1997; and PCT/US95/14692, filed Nov. 10, 1995).

Nucleic acids encoding fluorescent compounds that are fusions between a polypeptide including a phosphorylation site and a fluorescent protein moiety can be made by ligating nucleic acids that encode each of these. Nucleic acids encoding fluorescent compounds that include the amino acid sequence of a fluorescent protein moiety in which one or more amino acids in the amino acid sequence of a fluorescent protein moiety are substituted to create a substrate site for an activity can be created by, for example, site specific mutagenesis of a nucleic acid encoding a fluorescent protein moiety.

Nucleic acids used to transfect cells with sequences coding for expression of a polypeptide of interest such as those encoding a fluorescent compound generally will be in the form of an expression vector including expression control sequences operatively linked to a nucleotide sequence coding for expression of the polypeptide. As used herein, the term "nucleotide sequence coding for expression of a polypeptide" refers to a sequence that, upon transcription and translation of mRNA, produces the polypeptide. As any person skilled in the art recognizes, this includes all degenerate nucleic acid sequences encoding the same amino acid sequence. This can include sequences containing, e.g. introns. As used herein, the term "expression control sequences" refers to nucleic acid sequences that regulate the expression of a nucleic acid sequence to which it is operatively linked. Expression control sequences are "operatively linked" to a nucleic acid sequence when the expression control sequence control and regulate the transcription and, as appropriate, translation of the nucleic acid sequence. Thus, expression control sequences can include appropriate promoters, enhancers, transcription termination, or a start codon, (i.e., ATG) in front of a protein-encoding gene, splicing signals for introns, maintenance of the correct reading frame of that gene to permit proper translation of the mRNA, and stop codons. Recombinant nucleic acid can be incorporated into an expression vector comprising expression control sequences operatively linked to the recombinant eukaryotes by inclusion of appropriate promoters, replication sequences, market, etc. The expression vector can be transfected into a host cell for expression of the recombinant nucleic acid. Host cells can be selected for high levels of expression in order to purify the protein. *E. coli* is useful for this purpose. Alternatively, the host cell can be a prokaryotic or eukaryotic cell selected to study the activity of an enzyme produced by the cell. The cell can be, e.g. a cultured cell or a cell in vivo. The construction of expression vectors and the expression of genes in transfected cells involves the use of molecular cloning techniques also well known in the art (Sambrook et al., Molecular Cooing—A Laboratory Manual, Cold Spring Harbor Laboratory, Cold Spring Harbor, N.Y. (1989); Ausubel et la., Current Protocols in Molecular Biology, Greene Publishing Associates and John Wiley & Sons, Inc.).

Recombinant fluorescent protein substrates can be produced by expression of nucleic acid encoding for the protein in *E. coli*. Aequorea-related florescent proteins are best expressed by cells cultured between about 15° C. and 30° C. but higher temperatures (e.g. 37° C.) are possible. After synthesis, these enzymes are stable at higher temperatures (e.g., 37° C.) and can be used in assay at those temperatures.

The construct can also contain a tag to simplify isolation of the expressed fluorescent compound. For example, a polyistidine tag of, e.g. six histidine residues, can be incorporated at the amino or carboxyl terminal of the fluorescent compound. The polyhistidine tag allows convenient isolation of the protein in a single step by nickel chromatography.

Alternatively, the fluorescent compound, such as a fluorescent protein substrate, need not be isolated from the host cells. This method is particularly advantageous for the assaying for the presence of an activity in situ.

Methods for Determining Whether a Sample Contains an Activity

The present invention includes methods for determining whether a sample contains an activity using a fluorescent compound of the present invention. Depending on the type of activity to be determined, different fluorescent compounds are to be used. For example, if a protease activity is to be determined, then a fluorescent compound that is a substrate for a protease is used in the present methods. Likewise, if a protein kinase activity is to be determined, then a fluorescent compound that is a substrate for a protein kinase is used in the present invention.

The present method for determining whether a sample contains an activity comprises contacting a sample with a fluorescent compound of the present invention, wherein said fluorescent compound exhibits quenching. The sample is contacted with a quenching agent, excited, and the amount of emission from the fluorescent compound under quenching conditions is measured.

As is known in the art, different cofactors are required for different enzyme reactions. Thus, the skilled artisan would realize that such cofactors should be present in the assay conditions for those enzymes. For example, protein kinases add a phosphate residue to the phosphorylation site of a protein generally through the hydrolysis of ATP to ADP. Fluorescent compounds that are substrates for protein kinases are useful in assays to determine the amount of protein kinase activity in a sample. The assays of this invention take advantage of the fact that phosphorylation of the protein results in a change in a fluorescent property of the fluorescent compound that can be detected by quenching. Methods for determining whether a sample has kinase activity involve contacting the sample with a fluorescent compound having a phosphorylation site recognized by the protein kinase to be assayed and with a phosphate donor under selected test conditions. A phosphate donor is a compound containing a phosphate moiety that the kinase is able to use to phosphorylate the protein substrate. ATP (adenosine-5'-triphosphate) is by far the most common phosphate donor. In certain instances (such as whole cell studies) the sample will contain enough of a phosphate donor to make this step unnecessary. Then the fluorescent compound is excited with light in its excitation spectrum in the presence and absence of at least one quenching agent. If the fluorescent compound has been phosphorylated, the substrate will exhibit resistance to quenching, indicating that the sample contains protein kinase activity. These general methods can be used to detect any activity using fluorescent compound, assay conditions, and quenching conditions appropriate for an activity.

The amount of an activity in a sample can be determined by measuring the amount of quenching in the sample at a first time and a second time after contact between the sample and the fluorescent protein compound and determining the degree of change or the rate of change in a quenching. These results can be compared to those obtained with a control sample that does not contain the activity, or contains a known amount of activity. The amount of an activity in the sample can be calculated as a function of the difference in the determined amount of quenching at the two times. For example, the absolute amount of an activity can be calibrated using standards of activity determined for certain amounts of activity after certain amounts of time. The faster or larger the difference in the amount of quenching, the more activity is present in the sample. The skilled artisan would realize that proper controls should be used to validate any comparisons made with data obtained from the sample.

Fluorescence in a sample is measured using a fluorimeter. In general, excitation radiation from an excitation source having a first wavelength, passes through excitation optics. The excitation optics causes the excitation radiation to excite the sample. In response, fluorescent compounds in the sample emit radiation that has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation. This process can be miniaturized and automated to enable screening many thousand of compounds.

For example, comparisons can be made with a control sample known not to contain an activity, a control sample known to contain an activity (preferably in a known amount), a control sample representing background signal, or a control sample with or without test compounds.

The sample can be any sample, such as a sample of cells, tissue, organ, or fluid obtained from an organism (such as a mammalian, such as a human) or an extract obtained therefrom. Miniaturized arrays of samples attached to a matrix, such as a bead or solid support as they are known in the art or later developed, can be used in the present invention to detect fluorescence or other activity in a sample. A sample can also comprise cultured cells, culture fluid, or extracts or conditioned media obtained therefrom. The cells can be prokaryotic or eukaryotic, such as mammalian cells, such as human cells.

Methods of performing assays on fluorescent materials are well known in the art. (Lakowics, Principles of Fluorescence Spectroscopy, Plenum Press, N.Y. (1983); Herman, Fluorescence Microscopy of Living Cells in Culture, Part B, Methods in Cell Biology, volume 30, Academic Press, San Diego, pp. 219–243 (1989); Turro, Modem Molecular Photochemistry, Menlo Park, Calif., Benjamin/Cummings Publishing, pp. 296–361 (1978)).

In one embodiment, a cell is transiently or stably transfected with an expression vector encoding a fluorescent compound containing a substrate site for an activity to be assayed. This expression vector optionally includes controlling nucleotide sequences such as promoter or enhancing elements. The expression vector expresses the fluorescent compound that contains the substrate site for an activity to be detected. The activity to be assayed may either be intrinsic to the cell or may be introduced by stable transfection or transient co-transfection with another expression vector encoding the activity and optionally including controlling nucleotide sequences such as promoter or enhancer elements. The fluorescent compound and the activity preferably are located in the same cellular compartment so that they have more opportunity to come into contact. Membrane-bound or membrane-associated fluorescent compounds can also be used in this and any other method of the present invention. The amount of activity is then determined by measuring the fluorescence of the sample (which can contain whole cells) under quenching conditions, and comparison to appropriate controls, such as controls that either do not contain the activity, or contain a known amount of activity.

A contemplated variation of the above assay is to use the controlling nucleotide sequence to produce a sudden increase in the expression of either the fluorescent compound or the enzyme being assayed, for example, by inducing expression of the construct. Fluorescence after quenching can be monitored at one or more time intervals after the onset of increased expression. A large difference in the amount of fluorescence after quenching over time reflects a large amount or high efficiency of the activity. This kinetic determination has the advantage of minimizing any dependency of the assay on the basal or background levels of activity.

In another embodiment, the vector may be incorporated into an entire organism by standard transgenic or gene replacement techniques. An expression vector capable of expressing an activity optionally may be incorporated into the entire organism by standard transgenic or gene replacement techniques. Then, a sample from the organism containing the fluorescent compound is tested. For example, cell or tissue homogenates, individual cells, or samples of body fluids, such as blood, can be tested.

Screening Assays

The methods of the invention can be used in drug screening to determine whether a test compound alters an activity. In one embodiment, the assay is performed on a sample in vitro suspected of containing an activity. A sample containing a known amount of activity is mixed with a fluorescent compound of the invention and a test compound. The amount of the activity in the sample is then determined as above, for example by measuring the amount of fluorescence after quenching at a first and optionally second time after contact between the sample, the fluorescent compound, and the test compound and at least one quenching agent. Then the amount of activity in the presence of the test compound is compared with the activity in the absence of the test compound. A difference indicates that the test compound alters the activity. The activity can be increased, decreased, or unchanged by a test compound.

The present invention also includes a compound identified by any method of the present invention. Such compounds can be provided as a pharmaceutical composition in a pharmaceutically acceptable carrier as is set forth in U.S. patent application Ser. No. 09/030,578, filed Feb. 24, 1998. The present invention also includes a library of such compounds, which comprise two or more of such compounds provided either separately or in combination. The present invention also includes a system used to screen and identify compounds, such as set forth in U.S. patent application Ser. No. 08/858,016, filed May 16, 1997.

In another embodiment, the ability of a compound to alter an activity in vivo is determined. In an in vivo assay, cells transfected with an expression vector encoding a fluorescent compound, such as a fluorescent protein, of the invention are exposed to at least one amount of at least one test compound, and the fluorescence after quenching in each cell (individually or as a population) can be determined. Typically, the difference is calibrated against standard measurements (for example, in the presence or absence of test compounds) to yield an absolute amount of activity. A test compound that inhibits or blocks the activity or expression of an activity can be detected by a relative change in fluorescence after quenching. The cell can also be tranfected with an expression vector to coexpress the activity or an upstream signaling component such as a receptor, and the fluorescent compound. This method is useful for detecting signaling to an activity such as a protein kinase of interest from an upstream component of a signaling pathway. If a signal from an upstream molecule, for example a receptor (preferably in the presence of an agonist), is inhibited by a test compound, then the kinase activity will be inhibited as compared to controls incubated without the test compound. This provides a method for screening for compounds that affect cellular events (including receptor-ligand binding, protein-protein interaction, or kinase activation), and signal to the target kinase. This method can use cultured cells or extracts or conditioned media derived therefrom. This method can also use cells derived from an organism, such as a mammal, such as a human. Such cells can be derived from a tissue, organ or fluid. The sample can also comprise an extract of such cells.

This invention also provides kits containing a fluorescent compound and optionally cofactors for an activity. In one embodiment, the kit comprises at least one container holding the fluorescent compound and optionally a second container holding a cofactor or buffer. Optionally, the kit can comprise other reagents or labware to practice a method, such as a method of the present invention. The entire kit can be provided in a separate container, such as a box. This container can include instructions for use of the contents in a method of the present invention, or for other purposes.

Libraries of Candidate Substrates

This invention provides libraries of fluorescent compounds useful for the identification and characterization of sequences that can be recognized by an activity. Libraries of these fluorescent compounds can be screened to identify sequences that can be modified by activities of unknown or known substrate specificity, or to characterize differences in activity in, or from, diseased and normal cells, tissues, fluids, or extracts thereof.

As used herein, a "library" refers to a collection containing at least two different members, preferably greater than ten different members. Each member of a fluorescent compound library comprises a fluorescent protein moiety and a variable substrate site for an activity, wherein the variable substrate site for an activity is preferably located at or near the amino-or carboxy-terminus of the fluorescent protein moiety and has fewer than about fifty amino acids, preferably less than about fifteen amino acids. The variety of amino acid sequences for the fluorescent protein moiety is at the discretion of the artisan. For example, the library can contain a diverse collection of variable peptide moieties in which most or all of the amino acid positions are subjected to a non-zero but low probability of substitution. Also, the library can contain variable peptide moieties having an amino acid sequence in which only a few (e.g. one to ten) amino acid positions are varied, but the probability of substitution at each positions is relatively high.

Preferably, libraries of fluorescent compounds are created by expressing protein from libraries of recombinant nucleic acid molecules having expression control sequences operatively linked to nucleic acid sequences that code for the expression of different fluorescent compounds. Methods of making nucleic acid molecules encoding a diverse collection of peptides are described (U.S. Pat. No. 5,432,018 to Dower et al., U.S. Pat. No. 5,223,4098 to Ladner et al., U.S. Pat. No. 5,264,563 to Huse et al., and WO 92/06176 to Huse et al.) For expression of fluorescent compounds, recombinant nucleic acid molecules are used to tranfect cells, such that each cell contains a member of the library. This produces, in turn, a library of host cells capable of expressing the library of different fluorescent compounds. The library of host cells can be used in the screening methods of this invention to identify fluorescent compounds comprising a substrate site for an activity.

In one method of creating such a library, a diverse collection of oligonucleotides having preferably random codon sequences are combined to create polynucleotides encoding peptides having a desired number of amino acids. The oligonucleotides preferably are prepared by chemical synthesis. The polynucleotides encoding the variable peptide moieties can be coupled to the 5' end of a nucleic acid coding for the expression of a fluorescent compound or a carboxy-or amino-terminal portion of it. This is, the fluorescent protein moiety or a carboxy-terminal portion of it. This creates a recombinant nucleic acid molecule coding for the expression of a fluorescent compound having a peptide moiety fused to the amino- or carboxy-terminus of a fluorescent protein moiety. This recombinant nucleic acid molecule is then inserted into an expression vector to create a recombinant nucleic acid molecule comprising expression control sequences operatively linked to the sequence encoding the candidate substrate. The expression vector can then be inserted into an appropriate cell and expressed. To generate the collection of oligonucleotides which forms a series of codons encoding a random collection of amino acids and which is ultimately cloned into the vector, a codon motif is used, such as (NNK)x, where N may be A,C,G, or T (nominally equimolar, K is G or T (nominally equimolar), and x is the desired number of amino acids in the peptide moiety, e.g. 15 to produce a library of 15-mer peptides. The third positions may also be G or C, designated "S." Thus, NNK or NNS (i) code for all the amino acids, (ii) code for only one stop codon, and (iii) reduce the range of codon bias from 6:1 to 3:1. The expression of peptides from randomly generated mixtures of oligonucleotides in appropriate recombinant vectors is discussed in Olipant et al., Gene 44:177–183 (1986).

An exemplified codon motif (NNK)6 (SEQ ID NO:17) produces 32 codons, one for each of 12 amino acids, two for each of five amino acids, three for each of three amino acids and one (amber) stop codon. Although this motif produces a codon distribution as equitable as available with standard methods of oligonucleotide synthesis, it results in a bias against peptides containing one-codon residues.

An alternative approach to minimize the bias against one-codon residues involves the synthesis of 20 activated tri-nucleotides, each representing the codon for one of the 20 genetically encoded amino acids. These are synthesized by conventional means, removed from the support but maintaining the base and 5-OH-protecing groups, and activating by the addition of 3'O-phosphoramidite (and phosphate protection with beta-cyanoethyl groups) by the method used for the activation of mononucleosides, as generally described in McBride and Caruthers, Tetrahedron Letters 22:245 (1983). Degenerate "oligocodons" are prepared using these trimers and building blocks. The trimers are mixed at the desired molar rations and installed in the synthesizer. The ratios will usually be approximately equimolar, but may be controlled unequal ratios to obtain the over- to under-representation of certain amino acids coded for by the degenerate oligonucleotide collection. The condensation of the trimers to form the oligocodons is done essentially as described for conventional synthesis employing activated mononucleosides as building blocks (Atkinson and Smith, Oligonucleotide Synthesis, Gait ed. pp. 35–82 (1984). Thus, this procedure generates a population of oligonucleotides for cloning that is capable of encoding an equal distribution (or a controlled unequal distribution) of the possible peptide sequences.

Methods for Screening for Quenching Agents

The present invention includes methods for screening for agents that are quenching agents for a fluorescent compound of the present invention. As set forth in the Examples, fluorescent compounds that have a substrate site for an activity can exhibit quenching in the presence of a quenching agent. Preferable quenching agents and quenching conditions for a particular fluorescent compound can be followed by screening a plurality of quenching agents and quenching conditions following the methods set forth in the Examples. For example, a first sample of a fluorescent compound can be contacted with a control buffer and a second sample of a fluorescent compound can be contacted with an activity. These samples can be incubated for any period of time, such as between about one minute and 72 hours, preferably between 1 and 6 hours. Aliquots of these samples can then be contacted with test quenching agents and/or test quenching conditions, after which the fluorescence of these samples are measured. Samples that exhibit quenching can be readily identified by measuring the appropriate fluorescence from the samples (preferably by comparison with an appropriate control) which identify preferable quenching agents or quenching conditions. More preferable quenching agents or quenching conditions can be identified by reiterating this procedure using different concentrations of identified quenching agents for longer or shorter periods of time.

Methods for Screening Libraries of Candidate Substrates

Libraries of host cells expressing fluorescent compounds are useful in identifying fluorescent proteins having peptide moieties that exhibit quenching. Several methods of using the libraries are envisioned. In general, one begins with a library of recombinant host cells, each of which expresses a different fluorescent compound, such as fluorescent compound comprising a protein, peptide, or nucleic acid. Each cell is expanded into a clonal population that is genetically homogeneous.

In a first method, fluorescence quenching is measured or compared from each clonal population before and after at least one specified time after a known change in an intracellular activity. Alternatively, fluorescence quenching measured in each clonal population can be compared with the results obtained using untreated control cells. For example, a change in kinase activity could be produced by transfection with a gene encoding a kinase activity, by increasing the expression of the kinase using expression control elements, or by any condition that post-translationally modulates the kinase activity. Examples of the latter include cell surface receptor mediated elevation of intracellular cAMP to activate cAMP-dependent kinases, surface receptor mediated increases of intracellular cGMP to activate cGMP-dependent protein kinase, increases in cytosolic free calcium to activate $Ca^{2+}$/calmodulin-dependent protein kinase types I, II, or IV, or the production of diacylglycerol to activate protein kinase C, etc. One then selects for the clone(s) that show the largest or fastest changes in fluorescence in response to quenching compared to non-treated control cells.

EXAMPLES

A. Phosphorylation Sites Located in the Amino Acid Sequence of Aeguorea GFP Remote in the Primary Amino Acid Sequence Form the N-terminus Potential sites for phosphorylation were chosen at or close to positions in GFP that had previously been identified on the basis of mutagenesis experiments to exert significant effects on fluorescence, or which had a higher probability of surface exposure based on computer algorithms. For example, in mutant H9, Ser 202 and Thr 203 are mutated to Phe and Ile, respectively, creating a large change in spectral properties. Therefore, in one mutant, 199 RRLSI (SEQ ID NO:18), a potential site of phosphorylation was created around Ser 202, whose phosphorylation would significantly affect the fluorescent properties of the parent molecule. Similarly, the amino acids located at positions72 and 175 have been implicated in increased folding efficiency of GFP at higher temperatures and were made into potential sites of phosphorylation in separate mutants.

A complete list of the positions and amino acid changes made for each phosphorylation mutant in this series is outlined in FIG. 2. Proteins were expressed in E. Coli using the expression plasmid pRSET (Invitrogen, CA), in which the regions encoding GFP was fused in frame with nucleotides encoding an N-terminal polyhistidine tag (FIG. 3). The sequence changes were introduced by site-directed mutagenesis using the Bio-Rad mutagenesis kit (Kunkel, Proc. Natl. Acad. Sci. 82:488–492 (1985)); and Kunkel et al., Meth. Enzymol. 154:367–382 (1987)) and confirmed by sequencing. The recombinant proteins were induced with 0.05 mM IPTG, expressed in bacteria and purified by nickel affinity chromatography. The sequence changes, relative fluorescence, relative rater of phosphorylation and the percent change in fluorescence upon phosphorylation are listed in Table IV. In those cases where the protein exhibited no fluorescence after insertion of the phosphorylation site, no determinations were made on he effect of phosphorylation on fluorescence.

TABLE IV

Relative fluorescence, rate of phosphorylation and change in florescence upon phosphorylation for mutants incorporating phosphorylation sites remote from the N-terminus.

| SEQ ID NO: | Sequence | Fluorescence before phosphorylation (% of wild type) | Relative rates of phosphorylation | % change in fluorescence after incubation with kinase |
|---|---|---|---|---|
| SEQ ID NO. 19 | 25RRFSV | 95 | 1.75 | −5 |
| SEQ ID NO. 20 | 68RRFSR | 0 | N.D. | N.D. |
| SEQ ID NO. 14 | 68RRFSA | 6 | 0.6 | 10 |
| SEQ ID NO. 21 | 94RRSIF | 0 | N.D. | N.D. |
| SEQ ID NO. 22 | 131RRGSIL | 0 | N.D. | N.D. |
| SEQ ID NO. 23 | 155KRKSGI | 86 | 2.5 | 0 |
| SEQ ID NO. 24 | 172RRGSV | 90 | 1.57 | 0 |
| SEQ ID NO. 18 | 199RRLSI | 0 | N.D. | N.D. |
| SEQ ID NO. 15 | 214KRDSM | 21 | 1.88 | 40 |

N.D. means "not determined"

Numbers prior to the sequence indicate amino acid position in wild type GFP (SEQ ID NO:2) where phosphorylation motif starts. The relative rates of phosphorylation compare the rate of phosphorylation of the given phosphorylation motif with the endogenous protein kinase A phosphorylation motif in Aequorea GFP (HKFSV, SEQ ID NO:1) measured by incorporation of $^{32}$P after incubation of the purified substrate and protein kinase A catalytic subunit in the presence of $^{32}$P-labeled ATP using 3 micrograms of GFP, 5 micrograms protein kinase A catalytic subunit, for 10 minutes at 30° C. in standard phosphorylation buffer (20 mM MOPS, pH 6.5, 100 mM KCl, 100 micromolar ATP, 3 mM MgC$_2$, 1 mM DTT and 100 microCi $^{32}$P-labeled ATP. Reactions were terminated by blotting onto phosphocellulose paper and washing with 10% phosphoric acid. The percent change in fluorescence represents the increase in fluorescence (475 nm excitation, 510 nm emission) observed in each purified protein resulting from incubation with excess protein kinase A catalytic subunit for one hour at 30° C. using the same phosphorylation conditions as described above except that no 32P-labeled ATP was present and that after the reaction time was complete, samples were analyzed in a fluoromiter rather than blotted onto phosphocellulose paper.

The greatest change in fluorescence occurred in mutant 214KRDSM (SEQ ID NO:15) which exhibited at 40% change in fluorescence upon phophorylation. However, analysis of the kinetics of phosphorylation using gamma-$^{32}$P-labeled ATP demonstrated that the site is poorly phosphorylated by protein kinase A. Wild type GFP contains a mediocre consensus phosphorylation motif (25HKFSV, SEQ ID NO:1) that can be phosphorylated by protein kinase A in vitro with relatively slow kinetics. While phosphorylation at this position has no detectable effect on the fluorescence of GFP, the rate of phosphorylation at this position is used as an internal control between experiments to determine the relative rates of phosphorylation at sites engineered into the protein by site directed mutagenesis.

B. Phosphorylation Sites at or about the N-terminus of Aeguorea GFP

Phosphorylation sites at the N-terminus of GFP were engineered into S65T GFP by PCR. The sequence changes, relative fluorescence, relative rates of phosphorylation and the percent change in fluorescence upon phophorylation are tabulated in Table V.

TABLE V

Relative fluorescence, rate of phosphorylation and change in fluorescence upon phosphorylation for phosphorylation sites inserted at the N-terminus

| SEQ ID NO: | Sequence | Relative fluorescence as a % of wild type | Relative rates of phosphorylation | % Change in fluorescence |
|---|---|---|---|---|
| SEQ ID NO. 2 | 1MSKGEELF | 100 | 1.0 | 0 |
| SEQ ID NO. 25 | 1MRKGSCLF | 40 | 5.1 | 5.7 |
| SEQ ID NO. 26 | 1MRKGSLLF | 52 | 1.6 | 8.0 |
| SEQ ID NO. 27 | 1MRRESLLF | 30 | 3.0 | 6.0 |
| SEQ ID NO. 28 | 1MRDSCLF | 27 | 3.7 | 17 |
| SEQ ID NO. 29 | 1MSRRDSCF | 43 | 2.1 | 25 |
| SEQ ID NO. 30 | 1MSKRRDSL | 7 | 5.5 | 5.1 |

Numbers prior to the sequence indicate amino acid position in the wild type GFP where the phosphorylation motif starts. The relative rates of phosphorylation compare the rate of phosphorylation of the given phosphorylation motif with the endogenous protein kinase A phosphorylation motif in Aequorea GFP (HKFSV) measured by incorporation of $^{32}$P after incubation of the purified substrate and protein kinase A catalytic subunit in the presence of $^{32}$P-labeled ATP using the standard protocols described above. The percentage change in fluorescence represents the change in fluorescence (488 nm excitation, 511 nm emission) observed in each purified protein as a result of incubation with excess protein kinase A catalytic subunit for one hour at 30° C. using phosphorylation conditions described above. These results demonstrate that mutants whose sequence closely resembles the native protein retain considerable fluorescence, display good kinetics of phosphorylation, but show relatively small changes in fluorescence after phosphorylation. To improve the effect of phosphorylation on fluorescence, amino acids around the phosphorylation site were mutated to create an optimal phosphorylation sequence even if it disordered the existing local tertiary structure. Such disruption was predicted and found to decrease the basal fluorescence of these constructs in their non-phosphorylated state (Table VI).

TABLE VI

Relative fluorescence before phosphorylation and change in fluorescence upon phosphorylation for more drastically altered phosphorylation sites inserted at the N-terminus.

| SEQ ID NO: | Sequence | Relative fluorescence as a % of GFP mutant S65T | % Change in fluorescence upon phosphorylation |
|---|---|---|---|
| SEQ ID NO. 2 | 1MSKGEELF (WILD TYPE) | 100 | 0 |
| SEQ ID NO. 31 | 1MSRRRSI | 5.8 | 40 |
| SEQ ID NO. 32 | 1MRRRRSII | 5.1 | 70 |
| SEQ ID NO. 33 | −1MRRRRSIII | N.D | 43 |
| SEQ ID NO. 34 | −2MRRRRSIIIF | 0.7 | 15 |
| SEQ ID NO. 35 | −3MRRRRSIIIIF | 0.6 | 70 |

Numbers prior to the sequence indicate amino acid position in wild type GFP where the phosphorylation site starts. Negative numbers indicate extensions onto the wild-type N-terminus. The percent change in fluorescence represents the change in fluorescence (488 nm excitation, 511 nm emission) observed in each purified protein resulting from incubation with excess protein kinase A catalytic subunit for one hour at 30° C. using standard phosphorylation conditions described earlier.

Perhaps because of the reduced basal fluorescence, phosphorylation by protein kinase A produced greater percentage increases in fluorescence in these constructs than in the more conservative mutations of Table IV. Constructs 1MRRRRSII (SEQ ID NO:32), MRRRRSIII (SEQ ID NO:33) and –3MRRRRSIIIIF (SEQ ID NO:35) displayed the greatest increases, about 70%, in fluorescence upon phosphorylation using the standard phosphorylation conditions. However, these increased percentage increases were obtained at the cost of reduced ability to fold at higher temperatures and relatively poor fluorescence even after phosphorylation. To improve these characteristics, these mutants were further optimized by additional random mutagenesis with a novel selection procedure.

C. Further Optimization of N-terminal Phosphorylation Sites by Random Mutagenesis of the Remainder of GFP The two best constructs from above (1MRRRRSII (SEQ ID NO:32) and –3MRRRRSIIIIF (SEQ ID NO:35)) were further mutagenized and screened for variants that were highly fluorescent when phosphorylated, but weakly fluorescent when non-phosphorylated. The method involved expression of a randomly mutated fluorescent compound with or without simultaneous co-expression of the constitutively active catalytic subunit of protein kinase A in bacteria, and screening the individual mutants to determine those fluorescent compounds that are highly fluorescent in the presence but not the absence of the kinase.

Figure 4:
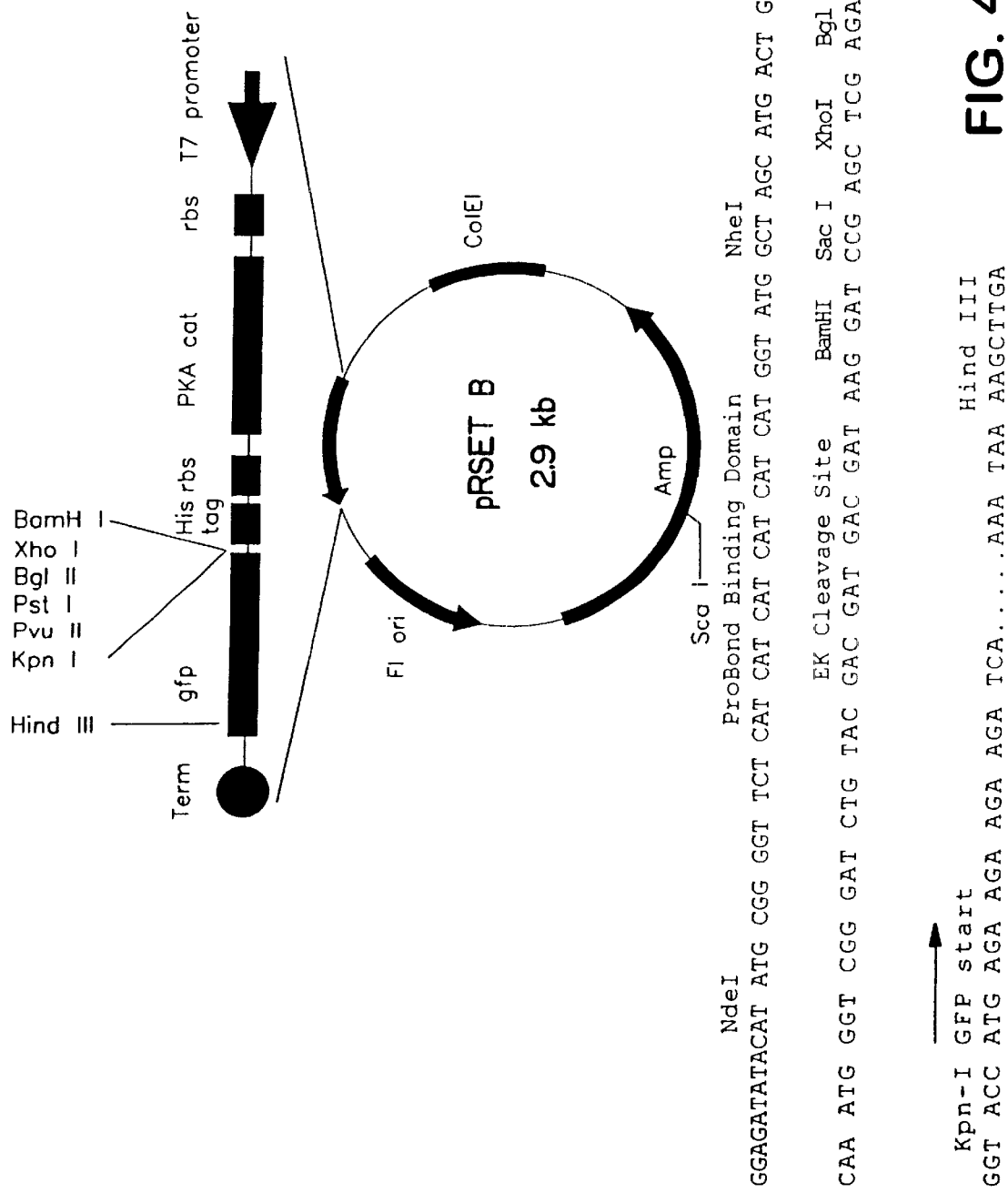
FIG. 4 depicts a duel expression vector having expression control sequences operably linked to sequences encoding for the expression of protein kinase A catalytic subunit (PKA cat) upstream from sequences coding for the expression of a fluorescent protein substrate.

To enable co-expression of the kinase and fluorescent compound such as GFP, a new expression vector with the kinase A catalytic subunit upstream from the fluorescent substrate was constructed (FIG. 4). This construct enabled expression of both the kinase and GFP from the same promoter through the insertion of a ribosome-binding site between the coding regions of the first and second genes. Random mutations were introduced into GFP by error-prone PCR and the resulting population of mutants cloned into the co-expression vector using the appropriate restriction sites. The expression library of vectors contained the mutated fluorescent compounds were transformed into host bacteria and individual bacterial colonies (each derived from a single cell, and hence containing a single unique mutant fluorescent compound) were cultured.

The colonies were screened for fluorescence either by fluorescence-activated cell sorting or by observation of individual colonies grown on an agar plate under a microscope. Those colonies that exhibited the greatest fluorescence were re-screened under conditions in which the kinase gene was inactivated. This was achieved in either of two ways. In the first method the co-expression vector was isolated and treated with restriction endonucleases and modifying enzymes (EcoRI, klenow fragment, and T4 DNA ligase) to cut the kinase gene, add additional bases and religate the DNA, causing a frame shift and hence inactivating the gene. The treated and non-treated plasmids were then re-transformed into bacteria and compared in fluorescence. Alternatively, the plasmids were initially grown in a RecA– (recombinase A negative) bacterial strain, where the kinase is stable, to screen for brighter mutants in the presence of the kinase. The plasmid DNA was then isolated and re-transformed into a strain of bacteria which is RecA+, in which the kinase is unstable and is lost through homologous recombination of the tandomly repeated ribosome biding sites (rbs). The bacteria have a strong tendency to eliminate the kinase A catalytic subunit because it slows their multiplication, so cells that splice out the kinase by recombination have a large growth advantage.

Comparison of the brightness of the mutant first in the presence of kinase then in its absence indicates the relative effect of phosphorylation on the mutant GFP fluorescence (after normalizing for GFP expression levels). A library of approximately $2 \times 10^6$ members was screened by this approach. Approximately 500 mutants displayed higher levels of fluorescence when screened in the presence of the kinase. After inactivation of the kinase, one mutant out of the 500 displayed reduced levels of fluorescence. The increased fluorescence of the remainder of the 500 mutants was independent of the presence of the kinase. This mutant GFP was isolated and sequenced and found to contain the following mutations compared to wild-type GFP (SEQ ID NO:2) (in addition to the N-terminal phosphorylation site 1MRRRRSII (SEQ ID NO:32)): S65A, N149K, V163A and I167T).

To confirm that this mutant was indeed directly sensitive to protein kinase A phosphorylation and to quantify its responsively, it was expressed in the absence of kinase. The *E. coli* were lysed and the protein purified as described earlier using a nickel affinity column. The protein exhibited high levels of fluorescence when induced at 30° C. but displayed reduced fluorescence when incubated at 37° C. After such preincubation (37° C. overnight) and separation of the less fluorescent material by centrifugation, this protein exhibited the largest change in fluorescence upon phosphorylation yet observed. The tolerance of this mutant for 37° C. treatment suggested that this mutant is suitable for use in mammalian cells.

D. GFP Mutants Exhibiting Phosphorylation Dependent Quenching

A phosphorylation recognition motif and substrate site for protein kinase A was engineered into the N-terminal region of GFP having the mutations S65A, N149K, V163A, and I167T (Examples A to C). Further mutations were made within the coding sequence of GFP at positions that were identified to be in close three-dimensional contact with the site of phosphorylation (phosphorylation site is at Glu5 in the wild type protein (SEQ ID NO:2)). These mutants were designed to strengthen ionic interactions between the phosphoserine and internal positively charged amino acids such as Lys79, for example by mutation of Lys79 to Arg or His. Additional mutations were also made to disorder the local N-terminal structure of the GFP in the non-phosphorylated form, for example, by disrupting the interactions between Lys3 and Glu90, by mutation of Glu90 to Lys or Asn. These mutations were made to both enhance the effect of phosphorylation on the fluorescent properties of GFP and to improve the accessibility of the phosphorylation motif or site to the kinase.

Mutation of amino acids close in sequence to the site of phosphorylation can also be changed to further weaken their interactions with other amino acid residues, although the sequence around the site of phosphorylation may directly impact the efficiency of phosphorylation by altering or disrupting the recognition motif for phosphorylation. An example of such a change is the mutation of Phe8 to the smaller and less hydrophobic amino acid Leu, which can disrupt or reduce hydrophobic interactions between Phe8 and Lys85, Cys70, Leu 19 and Met88. Also, mutation of Gly4 to Ala provides a relatively small hydrophobic amino acid that is preferred as a phosphorylation motif, and would not distort the interaction between the point of phosphorylation and its point of interaction within the GFP molecule. Not wishing to be bound to any mechanism of action, the inventors postulate that the phosphorylation of GFP may result in a transition from a locally disordered to ordered state without initially causing gross changes in protein conformation. This change can cause different fluorescent properties of the GFP in the phosphorylated and non-phosphorylated states under quenching conditions.

GFP mutant K4 (SEQ ID NO:49) (–2M, –1G,M1R,S2R, K3R,G4A,E5S,E6I,L7I,S65A,N149K,V163A,I167T) which contains a protein kinase A substrate recognition motif and substrate site for an activity, was used as the basis for other mutantsK5 to K16. Single mutants K79R (K5), E90N (K6), E90K (K7) and double mutants K79R/E90N (K8), K79R/E90K (K9), K79H, E90N (K10I), K79H, E90K (K11), K79H (K12), K79E, E90N (K13), K79E, E90K (K14), K79E (K15) and K79Q (K16) of K4 were made using known methods (see, Sambrook, Molecular Cloning, A Laboratory Manual, Cold Spring Harbor Press (1989)).

1. Use of Low pH as a Quenching Agent to Enhance Fluorescence Changes of GFP Mutants Upon Phosphorylation Mutants K4, K5, K6, K7, K8 and K9 were evaluated for fluorescence properties in their phosphorylated and non-phosphorylated states as a function of pH. Individual GFP mutants (4 micromolar) were phosphorylated by incubation with mouse recombinant protein kinase A catalytic subunit (Calbiochem #539–487, specific activity of 7,100 unit per milligram of protein) (1 unit in 20 mM MOPS, pH 7.3, 1 mM DTT, 3mM $MgCl_2$, 1 mM ATP at 30° C. for 1 hour in a total volume of 50 microliters). Control samples were incubated under the same conditions without protein kinase A. All fluorescence measurements were made using the Perseptive Biosystems 96 well plate reader with standard excitation and emission filters (Ex 485/25, Em 530/30) and gain setting of 70. Measurements were made approximately five minutes after addition of 100 microliters of the quenching buffer (50 mM citrate, 100 mM NaCl) provided at the indicated pH. The results represent the means of triplicate determinations. The fluorescence of the phosphorylated GFP mutant relative to the non-phosphorylated GFP mutant was calculated and presented in Table VII. These data demonstrate that mutants can exhibit changes in a fluorescent property upon quenching at low pH, and that their sensitivity to quenching is different for different mutants.

TABLE VII

Effect of pH on Quenching of GFP Mutants

Fold Change in Fluorescence of GFP in the Phosphorylated State at the Indicated pH Compared to Non-Phophorylated Samples

| Mutant | 5.6 | 5.4 | 5.2 | 5.0 | 4.8 |
| --- | --- | --- | --- | --- | --- |
| K4 | 0.84 | 0.86 | 0.91 | 1.04 | 1.92 |
| K5 | 1.0 | 1.0 | 1.05 | 1.6 | 1.9 |
| K6 | 1.0 | 1.0 | 1.0 | 1.6 | 2.5 |
| K7 | 0.95 | 0.95 | 1.0 | 1.4 | 2.0 |
| K8 | 0.90 | 0.90 | 1.0 | 1.4 | 2.8 |
| K9 | 1.0 | 1.0 | 1.0 | 1.3 | 2.3 |

The composition of the buffer used to stabilize the pH at the indicated value (for example, acetate, or citrate/phosphate) had little effect on quenching. Acetate buffers provided slightly greater and more robust changes than citrate. The highest degree of quenching in this example occurred using 100 mM acetate buffer in the presence of 100 mM NaCl at a volume that was twice that of the sample (standard quenching conditions). Preferred quenching conditions were dependent on the sample pH and the GFP mutant.

2. Effect of Time of Incubation and Low pH on Fluorescence of Phosphorylated and Non-Phosphorylated GFP Mutant K8

The time dependency of changes in quenching were investigated using GFP mutant K8 over a range of pH values using standard quenching buffer (Table VIII). The procedures described for the data presented in Table VII were used for these experiments, except that measurements were made at the indicated times. The "Time of Incubation" column represents the amount of time that the samples were under quenching conditions before fluorescence measurements were taken.

TABLE VIII

Effects of Time on Quenching of GFP Mutant K8

| Time of Incubation (hours) | Optimal pH | Fold Increase in Fluorescence of GFP in the Phosphorylated Sate |
| --- | --- | --- |
| 0 | 4.6 | 1.5 |
| 0.5 | 4.8 | 3.3 |
| 1.5 | 5.0 | 3.7 |
| 4.5 | 5.0 | 5.1 |
| 7.5 | 5.0 | 6.1 |
| 10.5 | 5.0 | 7.5 |

Figure 5:
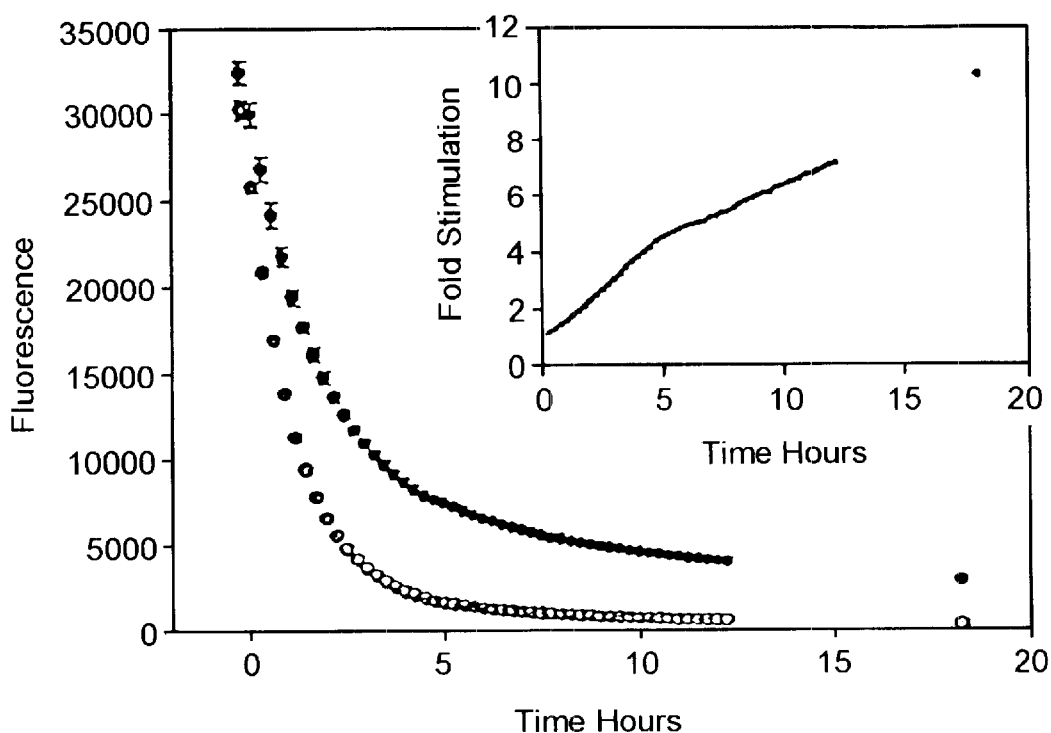
FIG. 5 depicts the effect of incubation time on the stability of GFP mutant K8 fluorescence after termination of a kinase reaction with 100 mM acetate buffer, 100 mM NaCl, 25 mM beta-glycerol phosphate pH 5.0.

Lower pH values of the quenching agent (for example, pH 4.6 or below) resulted in relatively smaller changes in fluorescence compared to control samples that were maximal relatively rapidly after addition of the quenching agent. Higher pH values (4.8 to 5.0) of the quenching agent resulted in larger differences in fluorescence, although these changes required larger times of incubation (up to ten hours). Maximal effects of quenching with low pH buffers were obtained around pH 5.0±0.2 with 100 mM acetate buffer with 100 mM NaCl. Maximal effects of low pH quenching were obtainable after ten to twenty-four hours, depending on the pH of the quenching agent used. After this time, fluorescence differences were stable for up to 72 hours. If the pH of the quenching agent (100 mM sodium acetate with 100 mM NaCl) was above pH 5.4, phosphorylation mediated fluorescence changes remained small, even up to 24 hours of incubation These results are summarized in FIG. 5.

Figure 6:
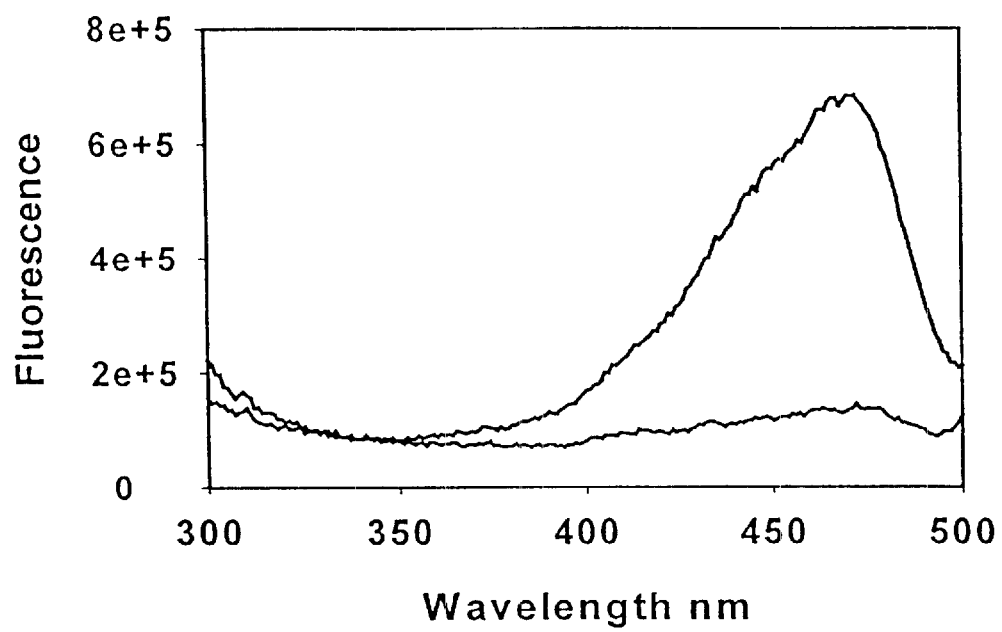
FIG. 6 depicts the effects of quenching on the fluorescent properties of the GFP mutant either after phosphorylation by protein kinase A or in the absence of protein kinase A.

Quenching with low pH buffer caused a decrease in the relative fluorescence of the non-phosphorylated GFP mutant K8 compared to the phosphorylated GFP mutant K8 (see FIG. 6).

3. Effect of Ionic Strength, Detergents, and Organic Solvents on Fluorescence of Phosphorylated and Non-Phosphorylated GFP Mutants The relative quenching of GFP mutant K8 in a phosphorylated and non-phosphorylated state was enhanced by the presence of 100 mM NaCl. Higher or lower concentrations of salt reduced the magnitude and kinetics of quenching for both phosphorylated and non-phosphorylated samples, but did enhance the relative difference in quenching between phosphorylated and non-phosphorylated samples. The inclusion of a divalent cation chelator such as EDTA or CDTA stabilized the fluorescence of phosphorylated GFP mutant K8, possibly by inhibiting acid phosphatases present as a contaminant in the sample or buffer. Beta-glycerol phosphate (Sigma) (25 mM) was also an effective inhibitor of acid phosphatase activities.

The detergents Triton® X-100, Tween® 20, NP-40 and CHAPS®(in the concentration range of 0.01 to 2 percent) in 100 mM acetate buffer, 100 mM NaCl, pH 4.6 to 9.0 reduced the fluorescence of both the phosphorylated and non-phosphorylated samples and increased the rate of loss of fluorescence of both the phosphorylated and non-phosphorylated samples. Based on these results, these quenching agents can be included in the quenching conditions to accelerate the rate of quenching which can make these assays more convenient.

Urea and guanidine HCl (up to a concentration of 3 M) at pH 7.0 did not significantly enhance the relative quenching of phosphorylated or non-phosphorylated GFP mutant K8.

Figure 7:
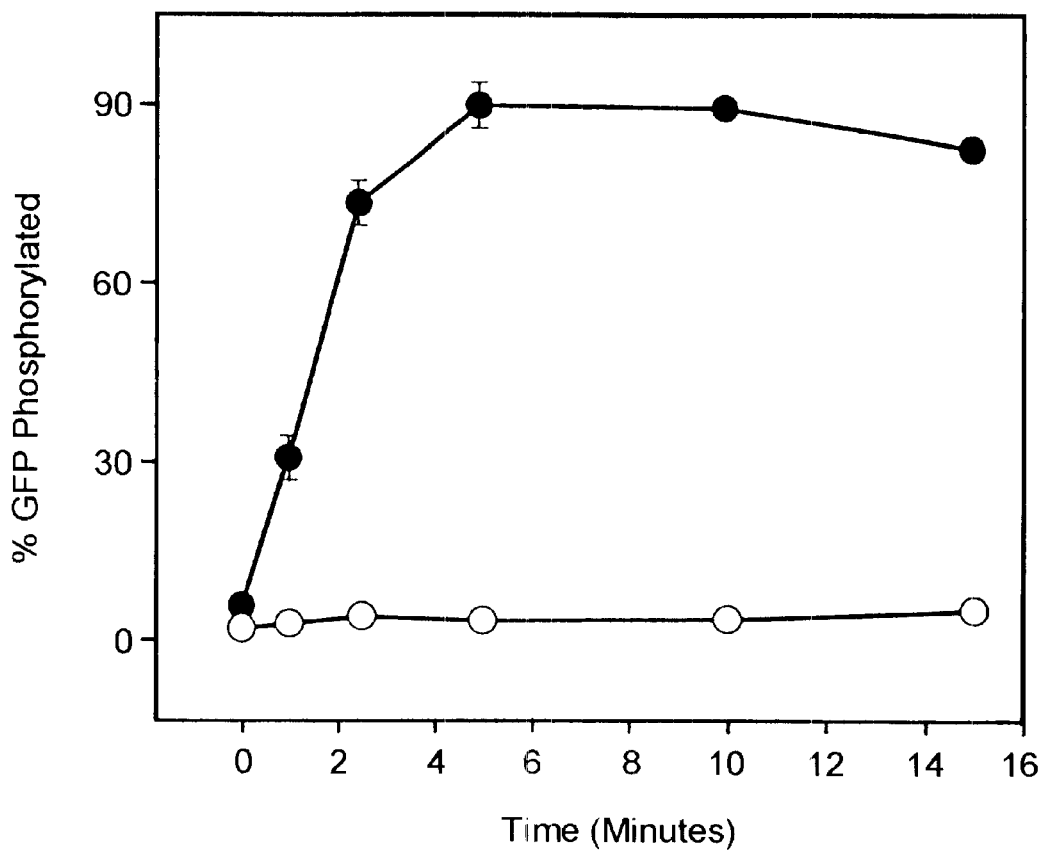
FIG. 7 depicts the kinetics of phosphorylation of a GFP having a kinase motif

4. Analysis of Phosphorylation Kinetics by Radiolabel-Based Measurements of Protein Phosphorylation The phosphorylation kinetics of GFP mutant K8 (-2M, -1G, M1R, S2R, K3R, G4A, E5S, E6I, L7I, S65A, K79R, E90N, N149K, V163A, I167T) and a control which lacked the N-terminal phosphorylation motif and site present in the mutant K8 were determined using the incorporation of $^{32}$P-phosphate (FIG. 7). Experiments were conducted using following reaction conditions: 20 mM MOPS, pH 7.4, 100 mM KCl, 0.2% Tween®20, 2.5 units of protein kinase A. Phosphorylation reactions were initiated by the addition of radiolabeled ATP and magnesium (5 $\mu$Ci $^{32}$P-ATP per tube) to GFP mutant K8 at a concentration of 2 micromolar. Phosphorylation reactions were performed for the indicated times at 30° C. and were terminated by the addition of 10% trichloroacetic acid (TCA). Bovine serum albumin was added as a carrier (10 microliters of 1% BSA per tube) and the resulting precipitate was collected by centrifugation. The resulting pellet was washed three times in 10% TCA prior to counting radioactivity by Cerenkov counting. The GFP mutant K8 exhibited greater incorporation of $^{32}$P than the control that lacks the N-terminal phosphorylation site. The results of these experiments demonstrate that the GFP mutant K8 is rapidly phosphorylated by protein kinase A.

Kinetic analysis of the rate of phosphorylation of GFP mutant K8 having the phosphorylation motif set forth in SEQ ID NO:49 measured by $^{32}$P incorporation revealed an apparent Km of 9 $\mu$M and a turnover number (Kcat) of 1.9 sec$^{-1}$ at 30° C. Analysis of these parameters based on quenching alone gave an estimated Km of 7.7 $\mu$M and Kcat of 1.2 sec$^{-1}$. Thus, both of these methods gave similar results, validating the use of quenching alone to determine these parameters and phosphorylation in general.

5. Validation of GFP Mutant K8 for Use in 96 Well Homogeneous Fluorescence-Based Kinase Assays The limit of detectability of protein kinase A using the GFP-based fluorescent assay set forth in these examples in a 96 well assay format was determined by measuring the fluorescence changes in response to incubation with a range of protein kinase A concentrations, as is described in Table VII. Reactions were performed under standard conditions for forty minutes at 30° C. Fluorescent measurements were made using a Cytofluor 2 series 4000 from Perspective Biosystem 96 well plate reader fitted with standard excitation and emission filters (485/25, 530/30) and set at a gain of 70. Assays were performed using Costar 96 well black plates with clear bottom in a reaction volume of 50 microliters. Reactions were terminated by addition of the preferred acetate quenching conditions (100 mM acetate buffer pH 5.0, 100 mM NaCl, 25 mM Beta-glycerol phosphate).

At the lowest concentration of PKA tested (26 pmol, or 0.5 ng) a detectable change in fluorescence signal was observed upon quenching. Fifty-two pmol of PKA gave an approximately two-fold increase in fluorescence compared to controls that were incubated in the absence of PKA. These results demonstrate that the assay provides highly sensitive measurements.

6. Detecting GFP Mutant K8 Using 96-well Plate Reader

These instrument settings and plates were used to determine the limit of detection of GFP mutant K8. In TRIS buffer at pH 8.0, the GFP mutant K8 was detectable above background fluorescence at approximately 0.1 $\mu$M. After treatment with the preferred quenching conditions at pH 5.0 GFP mutant K8 was detectable above background fluorescence at a limiting concentration of about about 0.5 $\mu$M. These results demonstrate that the GFP mutant K8 can be detected with high sensitivity using standard 96-well plate readers in a typical screening environment.

7. Robustness of the Assay to the Effects of Co-Solvents

Assay robustness to co-solvents is a highly desirable feature of drug screening systems because many drug candidates are not appreciably soluble in aqueous solutions. The co-solvents DMSO or ethanol are frequently used in drug screening at concentrations up to about 1% to dissolve drugs or target compounds. Thus, it is important to establish that these agents alone do not significantly influence the quenching of GFP at these concentrations. The preferred assay conditions as described above were used to determine the effects of the solvents DMSO and ethanol on the GFP mutant K8 phosphorylation assay.

DMSO or ethanol were added at 0, 0.01, 0.1, 0.2, 0.5, and 1.0% (Vol/Vol) to the kinase reaction mixture. At the maximum concentrations tested, these agents exhibited little or no effect of phosphorylation on the fluorescence development after quenching. These results establish that co-solvents such as DMSO or ethanol at concentrations used in screening assays do not interfere appreciably with GFP mutant K8 quenching assays.

8. Assay Validation with Protein Kinase A Inhibitors

Figure 8:
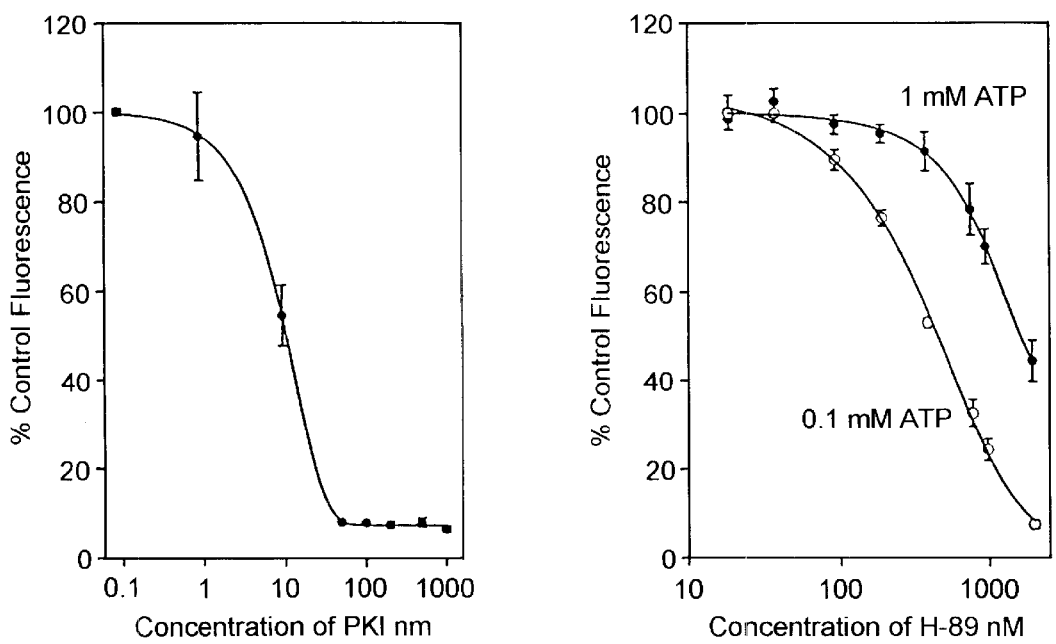
FIG. 8 depicts the determination of the dose dependent inhibition of PKA by known inhibitors of that enzyme using GFB mutant K8.

The protein kinase A inhibitors PKI (protein kinase A heat-stable inhibitor, isoform alpha (Calbiochem #539488) and H-89 (N-[2-((p-bromocinnamyl)amino)ethyl]-5-isoquinoline sulfonamide, HCl) (Calbiochem #371963) were tested in the preferred assay condition to determine if they could be detected using the GFP mutant K8 quenching assay. Both compounds were tested individually (between 0.1 and 1,000 nM) and pre-incubated with PKA in the absence of mutant K8 for 10 minutes at 4° C. Then, GFP mutant K8 was added to a final concentration of 4 $\mu$M and the mixtures were incubated for thirty minutes at 30° C. The kinase reactions were terminated by the addition of the preferred acetate quenching conditions (100 mM acetate, 100 mM NaCl, pH 5.0, 25 mM beta-glycerol phosphate). The fluorescence of these samples was measured 14 to 16 hours later. The results of these studies are presented in FIG. 8. The results of these studies establish that the GFP mutant K8 quenching assay can be used to detect kinase inhibitors and further validates the methodology for drug screening.

9. Detection of ATP Antagonists Using GFP Mutant K8 Quenching Assay

The protein kinase A inhibitor H-89 was tested in the GFP mutant K8 kinase assay at two different ATP concentrations (0.1 mM and 1 mM). In the presence of the higher ATP concentration, the inhibitor was much less efficient at inhibiting kinase activity. The response of the inhibitor to different ATP concentrations indicates that it acts by inhibiting ATP binding to the kinase active site. Because the GFP kinase assay can be performed at both high and low ATP concentrations, this method can be used to identify, measure, and detect ATP antagonists. Furthermore assay conditions can be established (i.e. the use of high or low ATP levels) to select for, or screen out, such compounds. This provides a significant improvement over competing assay technologies such as radioactive incorporation that can only be run at high sensitivity with low ATP concentrations. The results of these studies establish that the GFP mutant K8 quenching assay can be used to detect kinase inhibitors and further validates the methodology.

10. Use of GFP to Measure Other Kinase Activities

In addition to GFP mutant K8 having a PKA phosphorylation recognition motif, the inventors have made versions of GFP mutant K8 that have phosphorylation recognition motifs that are selective for protein kinase C (PKC) and mitogen activated protein kinase (MAP) (also known as extracellular regulated kinase (erk) (Table IX)). These substrates have the same site of phosphorylation as GFP mutant K8, which corresponds to Glu5 in the wild-type protein.

TABLE IX

Additional protein phosphorylation motifs introduced into GFP mutant K8.

| Kinase Specificity | Phosphorylation Motif | Clone Name | Relative Fluorescence Compared to GFP mutant K8 |
|---|---|---|---|
| Corresponding wild-type sequence | Met Ser Lys Gly Glu Glu Leu Phe (SEQ ID NO. 36) | Wild type | |
| Erk Kinase | Met Val Glu Pro Leu Thr Pro Ser Phe (SEQ ID NO. 64) | Erk-1 | 1.40 |
| Erk Kinase | Met Thr Gly Pro Leu Ser Pro Gly Phe (SEQ ID NO. 65) | Erk-4 | 1.49 |
| Erk Kinase | Met Thr Gly Pro Leu Ser Pro Gly Tyr (SEQ ID NO. 66) | Erk-5 | 1.26 |
| Erk Kinase | Met Thr Gly Pro Leu Ser Pro Gly Leu (SEQ ID NO. 67) | Erk-6 | 1.22 |
| Erk Kinase | Met Thr Gly Pro Leu Ser Pro Gly Pro (SEQ ID NO. 68) | Erk-7 | 0.40 |
| PKC α | Arg Arg Arg Arg Arg Lys Gly Ser Phe Arg (SEQ ID NO:56) | Pkc 3 | 0.72 |
| PKC α(+ Membrane association motif (hepta-Lys) at the C-terminus)) | Arg Arg Arg Arg Arg Lys Gly Ser Phe Arg (SEQ ID NO:57) | Pkc 3 lys | 0.95 |
| PKC β 1 | Phe Lys Leu Lys Arg Lys Gly Ser Phe Lys (SEQ ID NO:58) | Pkc 4 | 1.1.3 |
| PKC δ | Ala Arg Arg Lys Arg Lys Gly Ser Phe Phe (SEQ ID NO:59) | Pkc 5 | 1.91 |
| PKC ε | Tyr Tyr Ala Lys Arg Lys Met Ser Phe Phe (SEQ ID NO:60) | Pck 6 | 1.09 |
| PKC ζ | Arg Arg Phe Lys Arg Gln Gly Ser Phe Phe (SEQ ID NO:61) | Pkc 7 | 1.88 |
| PKC μ | Ala Ala Leu Val Arg Gln Met Ser Val Ala (SEQ ID NO:62) | Pkc 8 | 1.84 |

MAPKs (for mitogen-activated protein kinases) or ERKs (for extracellular-regulated kinases) selective phosphorylation motifs were introduced into GFP mutant K8 based on their known preferred substrate recognition motifs. Phosphorylation motifs were designed based on Songyang et al., Mo. Cell Biol. 16:6486–6493 (1996) and were made by replacing the protein kinase A phosphorylation motif in the GFP mutant Kg with the indicated phosphorylation motif using PCR methods known in the art. PKC isoform specific phosphorylation motifs were based on the sequences identified by Nishikawa et al. J. Biol. Chem. 272:952–960 (1997). These phosphorylation motifs were introduced into GFP mutant K8 by PCR as described above.

All of the constructs were successfully expressed at high level and were highly fluorescent (Table IX). The ERK substrates showed no substantial sequence identity with either the wild-type GFP or the PKA motifs present in GFP mutant K8, yet in most cases were as fluorescent or more fluorescent than GFP mutant K8. These results demonstrate that many different N-terminal phosphorylation motifs can be successfully introduced into GFP without significantly impacting GFP fluorescence.

E. Rates and Efficiencies of Phosphorylation of Additional GFP Substrate

1. Erk selective Substrates

Table X reports the phosphorylation rates of various GFP mutant sensors containing Erk s elective recognition motifs. The constructs Erk-6 and Erk-7 exhibited the greatest rates of phosphorylation. Kinetic analysis of the Erk-7 construct revealed a Km of 15 $\mu$M and a Kcat of 0.055 sec$^{-1}$.

TABLE X

Phosphorylation rates of various GFP Kinase Sensors

| Sample | $^{32}$P-Incorporation (CPM) |
|---|---|
| Control | 102 ± 32 |
| Myelin Basic Protein | 33361 ± 477 |
| Erk-1 | 1579 ± 282 |
| Erk-4 | 1982 ± 260 |
| Erk-5 | 6455 ± 558 |
| Erk-6 | 22498 ± 381 |
| Erk-6-B17 | 13,499 ± 472 |
| Erk-7 | 25502 ± 2077 |

These studies were performed by incubating GFP or MBP (myelin basic protein) (10 $\mu$M) with activated recombinant MAP kinase (Calbiochem #454855) (100 ng) for 30 minutes at 30° C. in buffer (20 mM MOPs, pH 7.2, 25 mM β-glycerol phosphate, 5 mM EGTA, 1 mM DTT, 0.1 mM ATP, 20 MM MgCl$_2$ 10 $\mu$Ci $^{32}$P-ATP in a volume of 50 microliters). Experiments were terminated and samples processed as described previously in subsection D.4. Results presented in Table X represent means of triplicate determinations±standard deviations of $^{32}$P-incorporation in washed pellets as described earlier.

The value of Kcat obtained for the GFP Erk substrate was similar to the Kcat values obtained for myelin basic protein, a well-characterized substrate of Erk kinase. These results demonstrate that Erk-1 selective phosphorylation motifs can be introduced into GFP and that the site of phosphorylation is rapidly and efficiently phosphorylated, with comparable kinetics to other proteins or peptides that are known substrates of Erk-1 kinases.

a. Mutagenesis of Erk Selective Substrates Erk-6 and Erk-7 to Improve Fluorescence and Kinetics of Phosphorylation To improve the fluorescent properties of the Erk kinase substrates (for example, Erk-6 and Erk-7), a library of mutants derived from these clones was made in which amino acids in the interior of the GFP that interact (with the three-dimensional structure of the protein) with the N-terminal region of GFP were mutated. The mutants were designed to produce a "better fit" of the Erk phosphorylation motif into the top of the barrel of GFP. This was achieved by enhancing the size of the positive charge associated around the site of phosphorylation (by mutation of K85 to R), pushing the backbone amide chain closer to the N-terminal phosphorylation recognition motif (by mutation of A87 to larger amino acids) and by making E90 more hydrophobic so that it could attract Pro 3 and therefore move closer to the phosphorylation motif. This library of mutants were screened for improved brightness and folding. Mutagenesis resulted in the creation of better folding, and a more fluorescent version, of the Erk-6 mutant, but did not significantly improve the fluorescence or folding of the Erk-7 mutant.

Selected clones from the Erk-6 and Erk-7 mutagenesis reactions were sequenced to confirmed that mutagenesis was successfully accomplished. The non-wild type sequences are displayed in TABLE XI. Therein, poorly fluorescent clones exhibited less than 10% of the fluorescence of GFP mutant K8 and were not further characterized. The GFP mutant Erk-6-B17 showed 158% of the fluorescence of GFP mutant K8, demonstrating that the mutagenesis approach was successful in improving GFP fluorescence.

TABLE XI

Mutants of Erk-6 and Erk-7 Substrates.

| Mutant Name | Mutations | Fluorescence |
|---|---|---|
| E6-B17 | A87T, E90A | Highly fluorescent |
| E6-A5 | K85R | Poorly Fluorescent |
| E6-A10 | K85R, A87T, E90L | Poorly Fluorescent |
| E6-A14 | K85R, A87V, E90P | Poorly Fluorescent |
| E6-A17 | K85R, A87T, E90S | Poorly Fluorescent |
| E7-B19 | E90I | Poorly Fluorescent |
| E7-B22 | A87T, E90R | Poorly Fluorescent |
| E7-A40 | K85R, A87T, E90N | Poorly Fluorescent |
| E7-A42 | K85R, A87T, E90P | Poorly Fluorescent | b. Effect of Phosphorylation on the Fluorescence Changes in GFP after Quench

Analysis of the effect of quenching on the fluorescence of the mutants Erk-6, Erk-7 and Erk-6-B17 was performed. The results presented in Table XII demonstrate improved fluorescent changes in response to quenching with acetate buffer. These results demonstrate that the mutagenesis approaches are generally applicable to improve fluorescence and phosphorylation dependent changes in quenching.

TABLE XII

Effects of quenching on the fluorescence of Erk-6 and Erk-7 mutants

| Constructs | Fold Increase in Fluorescence after Phosphorylation |
|---|---|
| Erk-6 | 1.20 |
| Erk-6-17B | 1.40 |
| Erk-7 | 1.05 |

These experiments were performed by incubating the GFP sample (2 μM) with Erk-1 kinase (1 μg) for 1 hour at 30° C. in assay buffer (20 mM MOPS, pH 7.2, 25 mM beta-glycoerol phosphate, 5 mM EGTA, 1 mM DTT, 1 mM ATP, 20 mM $MgCl_2$). Reactions were quenched by the addition of acetate quenching buffer (100 μL of 100 mM Acetate pH 5.0, 100 mM NaCl, 20 mM beta-Glycerol phosphate). Fluorescence changes were measured after 3 hours of incubation in acetate quenching buffer. Results represent the means of triplicate determinations.

The mutant Erk-6-B17 exhibited 1.4 times greater fluorescence than the original construct Erk-6. Incubation of this mutant with an excess activated kinase resulted in larger change in fluorescence after quenching. These results demonstrate that these methods of improving mutants are generally applicable to the creation and improvement of a range of phosphorylation motifs.

F. PKC Selective Phosphorylation Motifs

The rates of phosphorylation of GFP having PKC motifs were determined by measuring $^{32}P$ incorporation in the presence of different PKC isoforms (Table XIII). These examples include one example where a membrane association motif is part of the GFP mutant.

TABLE XIII

Rate of Phosphorylation of Various GFP Kinase Substrates Using Various Kinases

| GFP Mutant K8 Having the Indicated Phosphorylation Motif | Kinase and Activity (CPM) | | |
|---|---|---|---|
| | PKC alpha | PKC ε | PKC ζ |
| PKC alpha | 10,629 | 21,734 | 8,129 |
| PKC alpha + Membrane Association motif (Hepta-Lys) | 22,675 | 10,230 | 2,138 |
| PKC β 1 | 13,332 | 39,533 | 20,173 |
| PKC γ | 4,935 | 12,473 | 7,733 |
| PKC ε | 11,310 | 43,705 | 26,783 |
| PKC ζ | 4,745 | 12,688 | 8,421 |
| PKC μ | 5,230 | 20,259 | 14,606 |

These experiments were performed by incubating the indicated GFP mutant (5 micromolar) with the indicated PKC isoform (0.2 μg) for 30 minutes at 30° C. in 25 mM TRIS pH 7.5, 1 mM DTT, 10 mM $MgCl_2$ 0.1 mM ATP 20 μg/ml phosphatidylserine, 10 μM OAG, 200 μM $CaCl_2$ (for PKCα) and 1 mM EGTA (for PKCs ε and ζ). These results demonstrate that the available sequence diversity available at the N-terminus of GFP is sufficient to generate isoform specific phosphorylation of different mutants. The relative specificities identified for the GFP substrates in this experiment broadly matched those identified by Nishikawa et al (1997) who used non-GFP peptides to selectively measure PCK isoform activity. GFP contains an endogenous phosphorylation site (underlined) (Gly His Lys Phe <u>Ser</u> Val Ser Gly) within a relatively poorly recognized phosphorylation recognition motif that may be phosphorylated by some PKC isoforms. This may reduce the apparent specificity of the N-terminal phosphorylation motifs as measured by $^{32}P$-incorporation because these data represent phosphorylation both at the N-terminal site and the internal site. Membrane association motif poly-Lys (hepta-Lys) was added to the C-terminus of GFP mutant K8 with PKC alpha phosphorylation motif at the N-terminus.

1. Determination of Fluorescence Changes in Response to Phosphorylation

To determine if changes in fluorescence correlated with changes in phoshorylation, the previous experiments were repeated except that the fluorescence changes rather than $^{32}P$ incorporation were measured after the addition of a quenching agent. These results demonstrate that fluorescence changes in the GFP samples after quenching correlate with the incorporation of 32P (see Table XIV).

Maximal quenching for the PKC substrates was observed with 50 mM acetate buffer at pH 5.2 in the presence of 20% DMSO. The maximum change in fluorescence observed was typically 1.6 to 2.0 fold greater fluorescence for the phosphorylated substrate after 24 hours under the best conditions identified. The difference in quench conditions for the case of the PKC specific substrates compared to the PKA substrate may be due to the large hydrophobic motif C-terminal to the site of phosphorylation in these substrates (Ser-Phe-(Phe/Arg)-Phe).

2. Addition of Membrane Association and Protein-protein Interaction Motifs to GFP A polybasic membrane association motif derived from K-ras (Hancock et al. EMBO J. 12:4033–4039 (1991))) (Hepta-Lys) was added to the C-terminus of the PKC-alpha GFP by PCR. In addition, the farnesyl modification site could be added to the Hepta-Lys motif, resulting in the sequence Lys-Lys-Lys-Lys-Lys-Lys-Lys-Ser-Lys-Thr-Lys- Cys-Val-Ile-Met (SEQ ID NO:63) to create a tighter membrane association. The phosphorylation kinetics of this GFP was compared to that of a GFP that contained the PKC-alpha specific phosphorylation motif, but not the membrane associated motif. Both the constructs were highly fluorescent and were expressed at high levels in bacteria. The putative membrane associated GFP was soluble in aqueous solution at high salt concentration (0.3 M NaCl), but precipitated upon storage after dialysis to 0.1 M NaCl. All experiments using this protein were conducted on material that was stored in high salt and diluted into low ionic strength media in the presence of phospholipid vesicles immediately prior to experiments.

Figure 9:
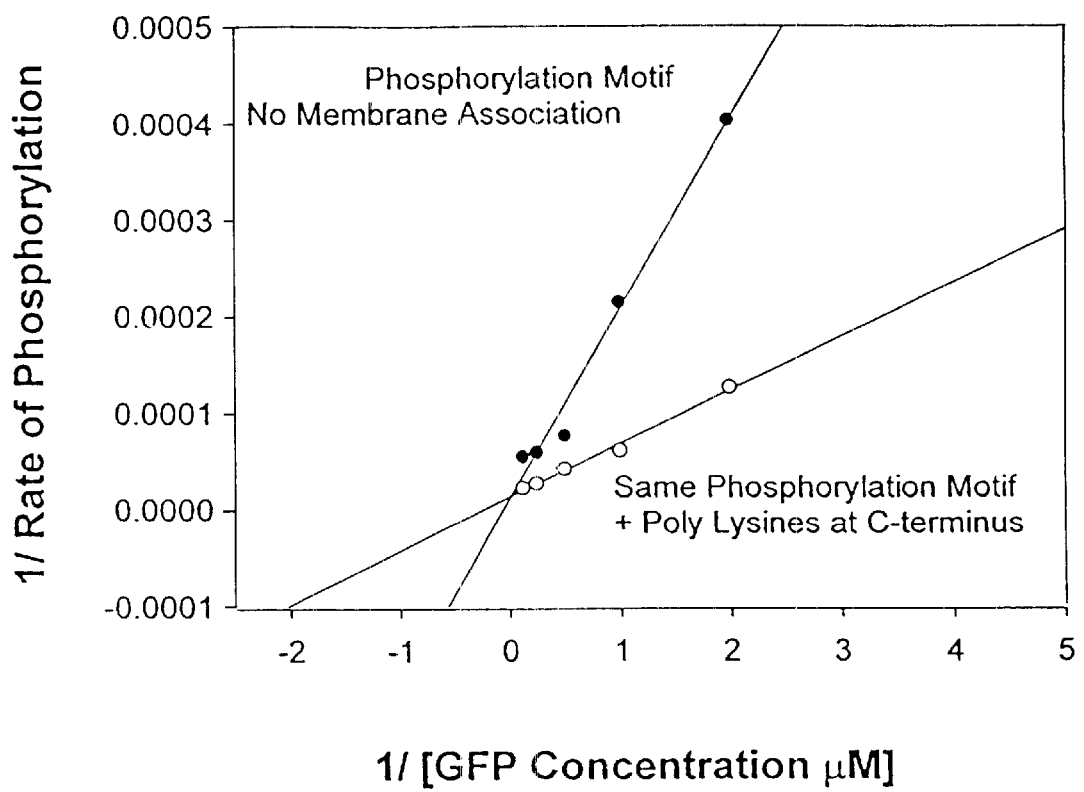
FIG. 9 depicts the phosphorylation of GFP with and without a membrane association motif.

The addition of a membrane association motif significantly increased the rate of phosphorylation of the substrate compared to a GFP substrate with the same phosphorylation recognition motif, but lacking the membrane association motif (FIG. 9). The addition of the membrane recognition motif also had a significant effect on the specificity of the PKC alpha with respect to other PKC isoforms (Table XIII). Kinetic analysis of the PKC alpha substrates with or without the membrane association motif reveals that increased phosphorylation was primarily due to an increase in apparent Km of the substrate, with little effect on the Vmax (FIG. 9).

All publications and patent documents cited in this application are incorporated by reference in their entirety for all purposes to the same extent as if each individual publication or patent document were so individually denoted.

I claim:

1. A fluorescent compound for detecting an activity, comprising:
an Aequorea fluorescent protein comprising the mutations S65A, K79R, E90N, N149K, V163A and I167T, and at least one exogenous N-terminal substrate recognition motif for an enzymatic activity,
wherein said Aequorea fluorescent protein has a contiguous sequence of 150 amino acids that has at least 85% sequence identity with an amino acid sequence, either contiguous or non-contiguous from the 238 amino acid wild type Aequorea green fluorescent protein of SEQ. ID. NO:2, wherein said at least one exogenous N-terminal substrate recognition motif is located within 20 amino acids of the amino terminus of said Aequorea fluorescent protein,
wherein said Aequorea fluorescent protein can be converted from a first state to a second state in response to said enzymatic activity,
wherein said enzymatic activity is selected from the group consisting of a kinase activity and a phosphatase activity, and
wherein said fluorescent compound exhibits at least one different fluorescent property in said first state compared to said second state when said first state and said second state are incubated in quenching conditions.

2. The fluorescent compound of claim 1, wherein said fluorescence property is fluorescence emission intensity.

3. The fluorescent compound of claim 1, wherein said quenching conditions is acid quenching.

4. The fluorescent compound of claim 1, wherein said fluorescent protein moiety comprises a phosphorylation recognition motif for a serine/threonine specific protein kinase.

5. The fluorescent compound of claim 4, wherein said phosphorylation recognition motif comprises a phosphorylation recognition motif for a protein kinase selected from the group consisting of protein kinase A, a cGMP-dependent protein kinase, protein kinase C, $Ca^{2+}$/calmodulin-dependent protein kinase I, $Ca^{2+}$/calmodulin-dependent protein kinase II, and MAP kinase activated protein kinase.

6. The fluorescent compound of claim 1, wherein said at least one N-terminal exogenous substrate recognition motif for an enzymatic activity is within the first 10 amino acid of the amino terminus of said Aequorea fluorescent protein.

7. The fluorescent compound of claim 1, wherein said Aequorea fluorescent protein is membrane associated.

8. The fluorescent compound of claim 1, wherein said Aequorea fluorescent protein comprises a poly-Lys region.

9. The fluorescent compound of claim 1, wherein said Aequorea fluorescent protein comprises a protein-protein interaction domain.

10. The fluorescent compound of claim 1, wherein said Aequorea fluorescent protein is membrane bound.

11. The fluorescent compound of claim 4, wherein said at least one N-terminal exogenous substrate recognition motif comprises the sequence Met Gly Arg Arg Arg Ala Ser Ile Ile (SEQ ID NO:49).

12. The fluorescent compound of claim 4, wherein said at least one N-terminal exogenous substrate recognition motif comprises the sequence Met Val Glu Pro Leu Thr Pro Ser Phe (SEQ ID NO:64).

13. The fluorescent compound of claim 4, wherein said at least one N-terminal exogenous substrate recognition motif comprises the sequence Met Thr Gly Pro Leu Ser Pro Gly Phe (SEQ ID NO:65).

14. The fluorescent compound of claim 4, wherein said at least one N-terminal exogenous substrate recognition motif comprises the sequence Met Thr Gly Pro Leu Ser Pro Gly Tyr (SEQ ID NO:66).

15. The fluorescent compound of claim 4, wherein said at least one N-terminal exogenous substrate recognition motif comprises the sequence Met Thr Gly Pro Leu Ser Pro Gly Leu (SEQ ID NO:67).

16. The fluorescent compound of claim 4, wherein said at least one N-terminal exogenous substrate recognition motif comprises the sequence Met Thr Gly Pro Leu Ser Pro Gly Pro (SEQ ID NO:68).

17. The fluorescent compound of claim 4, wherein said at least one N-terminal exogenous substrate recognition motif comprises the sequence Arg Arg Arg Arg Arg Lys Gly Ser Phe Arg (SEQ ID NO:56).

18. The fluorescent compound of claim 4, wherein said at least one N-terminal exogenous substrate recognition motif comprises the sequence Phe Lys Leu Lys Arg Lys Gly Ser Phe Lys (SEQ ID NO:58).

19. The fluorescent compound of claim 4, wherein said at least one N-terminal exogenous substrate recognition motif comprises the sequence Ala Arg Arg Lys Arg Lys Gly Ser Phe Phe (SEQ ID NO:59).

20. The fluorescent compound of claim 4, wherein said at least one N-terminal exogenous substrate recognition motif comprises the sequence Tyr Tyr Ala Lys Arg Lys Met Ser Phe Phe (SEQ ID NO:60).

21. The fluorescent compound of claim 4, wherein said at least one N-terminal exogenous substrate recognition motif comprises the sequence Arg Arg Phe Lys Arg Gln Gly Ser Phe Phe (SEQ ID NO:61).

22. The fluorescent compound of claim 4, wherein said at least one N-terminal exogenous substrate recognition motif comprises the sequence Ala Ala Leu Val Arg Gln Met Ser Val Ala (SEQ ID NO:62).

23. The fluorescent compound of claim 15, wherein said Aequorea-related fluorescent moiety further comprises the mutations A87T and E90A.

\* \* \* \* \*

SEQUENCE LISTING

<160> NUMBER OF SEQ ID NOS: 74

<210> SEQ ID NO 1
<211> LENGTH: 716
<212> TYPE: DNA
<213> ORGANISM: Aequorea
<220> FEATURE:
<221> NAME/KEY: CDS
<222> LOCATION: (1)..(714)

<400> SEQUENCE: 1

```
atg agt aaa gga gaa gaa ctt ttc act gga gtt gtc cca att ctt gtt        48
Met Ser Lys Gly Glu Glu Leu Phe Thr Gly Val Val Pro Ile Leu Val
1               5                   10                  15 gaa tta gat ggt gat gtt aat ggg cac aaa ttt tct gtc agt gga gag        96
Glu Leu Asp Gly Asp Val Asn Gly His Lys Phe Ser Val Ser Gly Glu
                20                  25                  30 ggt gaa ggt gat gca aca tac gga aaa ctt acc ctt aaa ttt att tgc       144
Gly Glu Gly Asp Ala Thr Tyr Gly Lys Leu Thr Leu Lys Phe Ile Cys
            35                  40                  45 act act gga aaa cta cct gtt cca tgg cca aca ctt gtc act act ttc       192
Thr Thr Gly Lys Leu Pro Val Pro Trp Pro Thr Leu Val Thr Thr Phe
        50                  55                  60 tct tat ggt gtt caa tgc ttt tca aga tac cca gat cat atg aaa cgg       240
Ser Tyr Gly Val Gln Cys Phe Ser Arg Tyr Pro Asp His Met Lys Arg
65                  70                  75                  80 cat gac ttt ttc aag agt gcc atg ccc gaa ggt tat gta cag gaa aga       288
His Asp Phe Phe Lys Ser Ala Met Pro Glu Gly Tyr Val Gln Glu Arg
                85                  90                  95 act ata ttt ttc aaa gat gac ggg aac tac aag aca cgt gct gaa gtc       336
Thr Ile Phe Phe Lys Asp Asp Gly Asn Tyr Lys Thr Arg Ala Glu Val
            100                 105                 110 aag ttt gaa ggt gat acc ctt gtt aat aga atc gag tta aaa ggt att       384
Lys Phe Glu Gly Asp Thr Leu Val Asn Arg Ile Glu Leu Lys Gly Ile
        115                 120                 125 gat ttt aaa gaa gat gga aac att ctt gga cac aaa ttg gaa tac aac       432
Asp Phe Lys Glu Asp Gly Asn Ile Leu Gly His Lys Leu Glu Tyr Asn
    130                 135                 140 tat aac tca cac aat gta tac atc atg gca gac aaa caa aag aat gga       480
Tyr Asn Ser His Asn Val Tyr Ile Met Ala Asp Lys Gln Lys Asn Gly
145                 150                 155                 160 atc aaa gtt aac ttc aaa att aga cac aac att gaa gat gga agc gtt       528
Ile Lys Val Asn Phe Lys Ile Arg His Asn Ile Glu Asp Gly Ser Val
                165                 170                 175
```

```
caa cta gca gac cat tat caa caa aat act cca att ggc gat ggc cct      576
Gln Leu Ala Asp His Tyr Gln Gln Asn Thr Pro Ile Gly Asp Gly Pro
            180                 185                 190 gtc ctt tta cca gac aac cat tac ctg tcc aca caa tct gcc ctt tcg      624
Val Leu Leu Pro Asp Asn His Tyr Leu Ser Thr Gln Ser Ala Leu Ser
                195                 200                 205 aaa gat ccc aac gaa aag aga gac cac atg gtc ctt ctt gag ttt gta      672
Lys Asp Pro Asn Glu Lys Arg Asp His Met Val Leu Leu Glu Phe Val
210                 215                 220 aca gct gct ggg att aca cat ggc atg gat gaa cta tac aaa ta           716
Thr Ala Ala Gly Ile Thr His Gly Met Asp Glu Leu Tyr Lys
225                 230                 235

<210> SEQ ID NO 2
<211> LENGTH: 238
<212> TYPE: PRT
<213> ORGANISM: Aequorea

<400> SEQUENCE: 2

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
        50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235

<210> SEQ ID NO 3
<211> LENGTH: 5
<212> TYPE: PRT
<213> ORGANISM: Artificial sequence
<220> FEATURE:
<223> OTHER INFORMATION: phosphorylation recognition motif for protein
      kinase A
<220> FEATURE:
<221> NAME/KEY: VARIANT
```

```
<222> LOCATION: (1)..(5)
<223> OTHER INFORMATION: Xaa at residue 3 is any amino acid
      Xaa at residue 5 is a hydrophobic amino acid

<400> SEQUENCE: 3

Arg Arg Xaa Ser Xaa
1               5

<210> SEQ ID NO 4
<211> LENGTH: 5
<212> TYPE: PRT
<213> ORGANISM: Artificial sequence
<220> FEATURE:
<223> OTHER INFORMATION: phosphorylation recognition motif for protein
      kinase A
<220> FEATURE:
<221> NAME/KEY: VARIANT
<222> LOCATION: (1)..(5)
<223> OTHER INFORMATION: Xaa at residue 3 is any amino acid
      Xaa at residue 5 is a hydrophobic amino acid

<400> SEQUENCE: 4

Arg Arg Xaa Thr Xaa
1               5

<210> SEQ ID NO 5
<211> LENGTH: 13
<212> TYPE: PRT
<213> ORGANISM: Artificial sequence
<220> FEATURE:
<223> OTHER INFORMATION: cGMP-dependent protein kinase phosphorylation
      recognition motif
<220> FEATURE:
<221> NAME/KEY: VARIANT
<222> LOCATION: (1)..(13)
<223> OTHER INFORMATION: Xaa is either lysine or arginine, and the first
      S is the site of phosphorylation

<400> SEQUENCE: 5

Xaa Lys Ile Ser Ala Ser Glu Phe Asp Arg Pro Leu Arg
1               5                   10

<210> SEQ ID NO 6
<211> LENGTH: 5
<212> TYPE: PRT
<213> ORGANISM: Artificial sequence
<220> FEATURE:
<223> OTHER INFORMATION: residues for the cGMP-dependent protein kinase
      phosphorylation recognition motif

<400> SEQUENCE: 6

Asp Arg Pro Leu Arg
1               5

<210> SEQ ID NO 7
<211> LENGTH: 8
<212> TYPE: PRT
<213> ORGANISM: Artificial sequence
<220> FEATURE:
<223> OTHER INFORMATION: synthetic substrates for protein kinase C
<220> FEATURE:
<221> NAME/KEY: variant
<222> LOCATION: (1)..(8)
<223> OTHER INFORMATION: Xaa is any amino acid

<400> SEQUENCE: 7

Xaa Arg Xaa Xaa Ser Xaa Arg Xaa
1               5
```

```
<210> SEQ ID NO 8
<211> LENGTH: 9
<212> TYPE: PRT
<213> ORGANISM: Artificial sequence
<220> FEATURE:
<223> OTHER INFORMATION: phosphorylation recognition motif

<400> SEQUENCE: 8

Lys Lys Lys Lys Arg Phe Ser Phe Lys
 1               5

<210> SEQ ID NO 9
<211> LENGTH: 9
<212> TYPE: PRT
<213> ORGANISM: Artificial sequence
<220> FEATURE:
<223> OTHER INFORMATION: phosphorylation recognition motif

<400> SEQUENCE: 9

Leu Arg Arg Leu Ser Asp Ser Asn Phe
 1               5

<210> SEQ ID NO 10
<211> LENGTH: 10
<212> TYPE: PRT
<213> ORGANISM: Artificial sequence
<220> FEATURE:
<223> OTHER INFORMATION: recognition sequence around the phosphorylation
      site

<400> SEQUENCE: 10

Lys Lys Leu Asn Arg Thr Leu Thr Val Ala
 1               5                  10

<210> SEQ ID NO 11
<211> LENGTH: 10
<212> TYPE: PRT
<213> ORGANISM: Artificial sequence
<220> FEATURE:
<223> OTHER INFORMATION: recognition sequence around the phosphorylation
      site

<400> SEQUENCE: 11

Lys Lys Ala Asn Arg Thr Leu Ser Val Ala
 1               5                  10

<210> SEQ ID NO 12
<211> LENGTH: 10
<212> TYPE: PRT
<213> ORGANISM: Artificial sequence
<220> FEATURE:
<223> OTHER INFORMATION: Substrate

<400> SEQUENCE: 12

Met Arg Arg Arg Arg Ser Ile Ile Thr Gly
 1               5                  10

<210> SEQ ID NO 13
<211> LENGTH: 13
<212> TYPE: PRT
<213> ORGANISM: Artificial sequence
<220> FEATURE:
<223> OTHER INFORMATION: substrate

<400> SEQUENCE: 13

Met Arg Arg Arg Arg Ser Ile Ile Ile Ile Phe Thr Gly
 1               5                  10
```

```
<210> SEQ ID NO 14
<211> LENGTH: 5
<212> TYPE: PRT
<213> ORGANISM: Artificial sequence
<220> FEATURE:
<223> OTHER INFORMATION: phosphorylation recognition motif

<400> SEQUENCE: 14

Arg Arg Phe Ser Ala
1               5

<210> SEQ ID NO 15
<211> LENGTH: 5
<212> TYPE: PRT
<213> ORGANISM: Artificial sequence
<220> FEATURE:
<223> OTHER INFORMATION: phosphorylation recognition motif

<400> SEQUENCE: 15

Lys Arg Asp Ser Met
1               5

<210> SEQ ID NO 16
<211> LENGTH: 9
<212> TYPE: PRT
<213> ORGANISM: Artificial sequence
<220> FEATURE:
<223> OTHER INFORMATION: phosphorylation motif

<400> SEQUENCE: 16

Met Ser Lys Arg Arg Asp Ser Leu Thr
1               5

<210> SEQ ID NO 17
<211> LENGTH: 3
<212> TYPE: DNA
<213> ORGANISM: Artificial sequence
<220> FEATURE:
<223> OTHER INFORMATION: randomly generated mixtures of oligonucleotides
<220> FEATURE:
<221> NAME/KEY: misc_feature
<222> LOCATION: (1)..(3)
<223> OTHER INFORMATION: n is A, C, G, or T, and k is G or T
      An exemplified codon motiff (NNK)6

<400> SEQUENCE: 17 nnk                                                                3

<210> SEQ ID NO 18
<211> LENGTH: 5
<212> TYPE: PRT
<213> ORGANISM: Artificial sequence
<220> FEATURE:
<223> OTHER INFORMATION: mutant

<400> SEQUENCE: 18

Arg Arg Leu Ser Ile
1               5

<210> SEQ ID NO 19
<211> LENGTH: 5
<212> TYPE: PRT
<213> ORGANISM: Artificial sequence
<220> FEATURE:
<223> OTHER INFORMATION: change in fluorescence for mutants

<400> SEQUENCE: 19
```

Arg Arg Phe Ser Val
1               5

<210> SEQ ID NO 20
<211> LENGTH: 5
<212> TYPE: PRT
<213> ORGANISM: Artificial sequence
<220> FEATURE:
<223> OTHER INFORMATION: change in fluorescence for mutants

<400> SEQUENCE: 20

Arg Arg Phe Ser Arg
1               5

<210> SEQ ID NO 21
<211> LENGTH: 5
<212> TYPE: PRT
<213> ORGANISM: Artificial sequence
<220> FEATURE:
<223> OTHER INFORMATION: change in fluorescence for mutants

<400> SEQUENCE: 21

Arg Arg Ser Ile Phe
1               5

<210> SEQ ID NO 22
<211> LENGTH: 6
<212> TYPE: PRT
<213> ORGANISM: Artificial sequence
<220> FEATURE:
<223> OTHER INFORMATION: change in fluorescence for mutants

<400> SEQUENCE: 22

Arg Arg Gly Ser Ile Leu
1               5

<210> SEQ ID NO 23
<211> LENGTH: 6
<212> TYPE: PRT
<213> ORGANISM: Artificial sequence
<220> FEATURE:
<223> OTHER INFORMATION: change in fluorescence for mutants

<400> SEQUENCE: 23

Lys Arg Lys Ser Gly Ile
1               5

<210> SEQ ID NO 24
<211> LENGTH: 5
<212> TYPE: PRT
<213> ORGANISM: Artificial sequence
<220> FEATURE:
<223> OTHER INFORMATION: change in fluorescence for mutants

<400> SEQUENCE: 24

Arg Arg Gly Ser Val
1               5

<210> SEQ ID NO 25
<211> LENGTH: 8
<212> TYPE: PRT
<213> ORGANISM: Artificial sequence
<220> FEATURE:
<223> OTHER INFORMATION: phosphorylation site inserted at the N-terminus

<400> SEQUENCE: 25

Met Arg Lys Gly Ser Cys Leu Phe

-continued

```
1               5

<210> SEQ ID NO 26
<211> LENGTH: 8
<212> TYPE: PRT
<213> ORGANISM: Artificial sequence
<220> FEATURE:
<223> OTHER INFORMATION: phosphorylation site inserted at the N-terminus

<400> SEQUENCE: 26

Met Arg Lys Gly Ser Leu Leu Phe
1               5

<210> SEQ ID NO 27
<211> LENGTH: 8
<212> TYPE: PRT
<213> ORGANISM: Artificial sequence
<220> FEATURE:
<223> OTHER INFORMATION: phosphorylation site inserted at the N-terminus

<400> SEQUENCE: 27

Met Arg Arg Glu Ser Leu Leu Phe
1               5

<210> SEQ ID NO 28
<211> LENGTH: 7
<212> TYPE: PRT
<213> ORGANISM: Artificial sequence
<220> FEATURE:
<223> OTHER INFORMATION: phosphorylation site inserted at the N-terminus

<400> SEQUENCE: 28

Met Arg Asp Ser Cys Leu Phe
1               5

<210> SEQ ID NO 29
<211> LENGTH: 8
<212> TYPE: PRT
<213> ORGANISM: Artificial sequence
<220> FEATURE:
<223> OTHER INFORMATION: phosphorylation site inserted at the N-terminus

<400> SEQUENCE: 29

Met Ser Arg Arg Asp Ser Cys Phe
1               5

<210> SEQ ID NO 30
<211> LENGTH: 8
<212> TYPE: PRT
<213> ORGANISM: Artificial sequence
<220> FEATURE:
<223> OTHER INFORMATION: phosphorylation site inserted at the N-terminus

<400> SEQUENCE: 30

Met Ser Lys Arg Arg Asp Ser Leu
1               5

<210> SEQ ID NO 31
<211> LENGTH: 7
<212> TYPE: PRT
<213> ORGANISM: Artificial sequence
<220> FEATURE:
<223> OTHER INFORMATION: phosphorylation site inserted at the N-terminus

<400> SEQUENCE: 31

Met Ser Arg Arg Arg Ser Ile
1               5
```

<210> SEQ ID NO 32
<211> LENGTH: 8
<212> TYPE: PRT
<213> ORGANISM: Artificial sequence
<220> FEATURE:
<223> OTHER INFORMATION: phosphorylation site inserted at the N-terminus

<400> SEQUENCE: 32

Met Arg Arg Arg Arg Ser Ile Ile
1               5

<210> SEQ ID NO 33
<211> LENGTH: 9
<212> TYPE: PRT
<213> ORGANISM: Artificial sequence
<220> FEATURE:
<223> OTHER INFORMATION: phosphorylation site inserted at the N-terminus

<400> SEQUENCE: 33

Met Arg Arg Arg Arg Ser Ile Ile Ile
1               5

<210> SEQ ID NO 34
<211> LENGTH: 10
<212> TYPE: PRT
<213> ORGANISM: Artificial sequence
<220> FEATURE:
<223> OTHER INFORMATION: phosphorylation site inserted at the N-terminus

<400> SEQUENCE: 34

Met Arg Arg Arg Arg Ser Ile Ile Ile Phe
1               5                   10

<210> SEQ ID NO 35
<211> LENGTH: 11
<212> TYPE: PRT
<213> ORGANISM: Artificial sequence
<220> FEATURE:
<223> OTHER INFORMATION: phosphorylation site inserted at the N-terminus

<400> SEQUENCE: 35

Met Arg Arg Arg Arg Ser Ile Ile Ile Ile Phe
1               5                   10

<210> SEQ ID NO 36
<211> LENGTH: 8
<212> TYPE: PRT
<213> ORGANISM: Artificial sequence
<220> FEATURE:
<223> OTHER INFORMATION: phosphorylation motif

<400> SEQUENCE: 36

Met Ser Lys Gly Glu Glu Leu Phe
1               5

<210> SEQ ID NO 37
<211> LENGTH: 8
<212> TYPE: PRT
<213> ORGANISM: Artificial sequence
<220> FEATURE:
<223> OTHER INFORMATION: HIV-1 protease

<400> SEQUENCE: 37

Ser Gln Asn Tyr Pro Ile Val Gln
1               5

<210> SEQ ID NO 38
<211> LENGTH: 9
<212> TYPE: PRT
<213> ORGANISM: Artificial sequence
<220> FEATURE:
<223> OTHER INFORMATION: HIV-1 protease

<400> SEQUENCE: 38

Lys Ala Arg Val Leu Ala Glu Met Ser
1               5

<210> SEQ ID NO 39
<211> LENGTH: 10
<212> TYPE: PRT
<213> ORGANISM: Artificial sequence
<220> FEATURE:
<223> OTHER INFORMATION: prohormone convertase

<400> SEQUENCE: 39

Pro Ser Pro Arg Glu Gly Lys Arg Ser Tyr
1               5                   10

<210> SEQ ID NO 40
<211> LENGTH: 5
<212> TYPE: PRT
<213> ORGANISM: Artificial sequence
<220> FEATURE:
<223> OTHER INFORMATION: interleukin-1b-converting enzyme

<400> SEQUENCE: 40

Tyr Val Ala Asp Gly
1               5

<210> SEQ ID NO 41
<211> LENGTH: 8
<212> TYPE: PRT
<213> ORGANISM: Artificial sequence
<220> FEATURE:
<223> OTHER INFORMATION: Adenovirus endopeptidase

<400> SEQUENCE: 41

Met Phe Gly Gly Ala Lys Lys Arg
1               5

<210> SEQ ID NO 42
<211> LENGTH: 10
<212> TYPE: PRT
<213> ORGANISM: Artificial sequence
<220> FEATURE:
<223> OTHER INFORMATION: cytomegalovirus assemblin

<400> SEQUENCE: 42

Gly Val Val Met Ala Ser Ser Arg Leu Ala
1               5                   10

<210> SEQ ID NO 43
<211> LENGTH: 10
<212> TYPE: PRT
<213> ORGANISM: Artificial sequence
<220> FEATURE:
<223> OTHER INFORMATION: Leishmanolysin

<400> SEQUENCE: 43

Leu Ile Ala Tyr Ile Leu Lys Lys Ala Thr
1               5                   10

```
<210> SEQ ID NO 44
<211> LENGTH: 7
<212> TYPE: PRT
<213> ORGANISM: Artificial sequence
<220> FEATURE:
<223> OTHER INFORMATION: b-Secretase for amyloid precursor protein

<400> SEQUENCE: 44

Val Lys Met Asp Ala Glu Phe
1               5

<210> SEQ ID NO 45
<211> LENGTH: 17
<212> TYPE: PRT
<213> ORGANISM: Artificial sequence
<220> FEATURE:
<223> OTHER INFORMATION: thrombin

<400> SEQUENCE: 45

Phe Leu Ala Glu Gly Gly Gly Val Arg Gly Pro Arg Val Val Glu Arg
1               5                   10                  15

His

<210> SEQ ID NO 46
<211> LENGTH: 13
<212> TYPE: PRT
<213> ORGANISM: Artificial sequence
<220> FEATURE:
<223> OTHER INFORMATION: renin and angiotension-converting enzyme

<400> SEQUENCE: 46

Asp Arg Val Tyr Ile His Pro Phe His Leu Val Ile His
1               5                   10

<210> SEQ ID NO 47
<211> LENGTH: 8
<212> TYPE: PRT
<213> ORGANISM: Artificial sequence
<220> FEATURE:
<223> OTHER INFORMATION: cathepsin D

<400> SEQUENCE: 47

Lys Pro Ala Leu Phe Phe Arg Leu
1               5

<210> SEQ ID NO 48
<211> LENGTH: 30
<212> TYPE: PRT
<213> ORGANISM: Artificial sequence
<220> FEATURE:
<223> OTHER INFORMATION: Kininogenases including kallikrein

<400> SEQUENCE: 48

Gln Pro Leu Gly Gln Thr Ser Leu Met Lys Arg Pro Pro Gly Phe Ser
1               5                   10                  15

Pro Phe Arg Ser Val Gln Val Met Lys Thr Gln Glu Gly Ser
                20                  25                  30

<210> SEQ ID NO 49
<211> LENGTH: 240
<212> TYPE: PRT
<213> ORGANISM: GFP mutant K4

<400> SEQUENCE: 49

Met Gly Arg Arg Arg Ala Ser Ile Ile Phe Thr Gly Val Val Pro Ile
1               5                   10                  15
```

```
Leu Val Glu Leu Asp Gly Asp Val Asn Gly His Lys Phe Ser Val Ser
            20                  25                  30

Gly Glu Gly Glu Gly Asp Ala Thr Tyr Gly Lys Leu Thr Leu Lys Phe
            35                  40                  45

Ile Cys Thr Thr Gly Lys Leu Pro Val Pro Trp Pro Thr Leu Val Thr
 50                  55                  60

Thr Phe Ala Tyr Gly Val Gln Cys Phe Ser Arg Tyr Pro Asp His Met
 65                  70                  75                  80

Lys Arg His Asp Phe Phe Lys Ser Ala Met Pro Glu Gly Tyr Val Gln
                 85                  90                  95

Glu Arg Thr Ile Phe Phe Lys Asp Asp Gly Asn Tyr Lys Thr Arg Ala
            100                 105                 110

Glu Val Lys Phe Glu Gly Asp Thr Leu Val Asn Arg Ile Glu Leu Lys
            115                 120                 125

Gly Ile Asp Phe Lys Glu Asp Gly Asn Ile Leu Gly His Lys Leu Glu
130                 135                 140

Tyr Asn Tyr Asn Ser His Lys Val Tyr Ile Met Ala Asp Lys Gln Lys
145                 150                 155                 160

Asn Gly Ile Lys Ala Asn Phe Lys Thr Arg His Asn Ile Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asn His Tyr Leu Ser Thr Gln Ser Ala
            195                 200                 205

Leu Ser Lys Asp Pro Asn Glu Lys Arg Asp His Met Val Leu Leu Glu
            210                 215                 220

Phe Val Thr Ala Ala Gly Ile Thr His Gly Met Asp Glu Leu Tyr Lys
225                 230                 235                 240

<210> SEQ ID NO 50
<211> LENGTH: 9
<212> TYPE: PRT
<213> ORGANISM: Artificial sequence
<220> FEATURE:
<223> OTHER INFORMATION: Cyclin B-CDC2

<400> SEQUENCE: 50

His His His Lys Ser Pro Arg Arg
1               5

<210> SEQ ID NO 51
<211> LENGTH: 9
<212> TYPE: PRT
<213> ORGANISM: Artificial sequence
<220> FEATURE:
<223> OTHER INFORMATION: cyclin A-CDK2

<400> SEQUENCE: 51

His His His Arg Ser Arg Pro Lys Arg
1               5

<210> SEQ ID NO 52
<211> LENGTH: 9
<212> TYPE: PRT
<213> ORGANISM: Artificial sequence
<220> FEATURE:
<223> OTHER INFORMATION: protein kinase A

<400> SEQUENCE: 52
```

```
Arg Arg Arg Arg Ser Ile Ile Phe Ile
1               5

<210> SEQ ID NO 53
<211> LENGTH: 9
<212> TYPE: PRT
<213> ORGANISM: Artificial sequence
<220> FEATURE:
<223> OTHER INFORMATION: SLK 1

<400> SEQUENCE: 53

Arg Arg Phe Gly Ser Leu Arg Arg Leu
1               5

<210> SEQ ID NO 54
<211> LENGTH: 9
<212> TYPE: PRT
<213> ORGANISM: Artificial sequence
<220> FEATURE:
<223> OTHER INFORMATION: ERK 1

<400> SEQUENCE: 54

Thr Gly Pro Leu Ser Pro Gly Pro Phe
1               5

<210> SEQ ID NO 55
<211> LENGTH: 13
<212> TYPE: PRT
<213> ORGANISM: Artificial sequence
<220> FEATURE:
<223> OTHER INFORMATION: protein kinase C alpha

<400> SEQUENCE: 55

Arg Arg Arg Arg Arg Lys Gly Ser Phe Arg Arg Lys Ala
1               5                   10

<210> SEQ ID NO 56
<211> LENGTH: 10
<212> TYPE: PRT
<213> ORGANISM: Artificial sequence
<220> FEATURE:
<223> OTHER INFORMATION: Phosphorylation motif

<400> SEQUENCE: 56

Arg Arg Arg Arg Arg Lys Gly Ser Phe Arg
1               5                   10

<210> SEQ ID NO 57
<211> LENGTH: 10
<212> TYPE: PRT
<213> ORGANISM: Artificial sequence
<220> FEATURE:
<223> OTHER INFORMATION: Phosphorylation motif

<400> SEQUENCE: 57

Arg Arg Arg Arg Arg Lys Gly Ser Phe Arg
1               5                   10

<210> SEQ ID NO 58
<211> LENGTH: 10
<212> TYPE: PRT
<213> ORGANISM: Artificial sequence
<220> FEATURE:
<223> OTHER INFORMATION: Phosphorylation motif

<400> SEQUENCE: 58

Phe Lys Leu Lys Arg Lys Gly Ser Phe Lys
```

```
1               5                    10
```

<210> SEQ ID NO 59
<211> LENGTH: 10
<212> TYPE: PRT
<213> ORGANISM: Artificial sequence
<220> FEATURE:
<223> OTHER INFORMATION: Phosphorylation motif

<400> SEQUENCE: 59

```
Ala Arg Arg Lys Arg Lys Gly Ser Phe Phe
1               5                    10
```

<210> SEQ ID NO 60
<211> LENGTH: 10
<212> TYPE: PRT
<213> ORGANISM: Artificial sequence
<220> FEATURE:
<223> OTHER INFORMATION: Phosphorylation motif

<400> SEQUENCE: 60

```
Tyr Tyr Ala Lys Arg Lys Met Ser Phe Phe
1               5                    10
```

<210> SEQ ID NO 61
<211> LENGTH: 10
<212> TYPE: PRT
<213> ORGANISM: Artificial sequence
<220> FEATURE:
<223> OTHER INFORMATION: Phosphorylation motif

<400> SEQUENCE: 61

```
Arg Arg Phe Lys Arg Gln Gly Ser Phe Phe
1               5                    10
```

<210> SEQ ID NO 62
<211> LENGTH: 10
<212> TYPE: PRT
<213> ORGANISM: Artificial sequence
<220> FEATURE:
<223> OTHER INFORMATION: Phosphorylation motif

<400> SEQUENCE: 62

```
Ala Ala Leu Val Arg Gln Met Ser Val Ala
1               5                    10
```

<210> SEQ ID NO 63
<211> LENGTH: 15
<212> TYPE: PRT
<213> ORGANISM: Artificial sequence
<220> FEATURE:
<223> OTHER INFORMATION: hepta-lys motif

<400> SEQUENCE: 63

```
Lys Lys Lys Lys Lys Lys Lys Ser Lys Thr Lys Cys Val Ile Met
1               5                    10                  15
```

<210> SEQ ID NO 64
<211> LENGTH: 9
<212> TYPE: PRT
<213> ORGANISM: Artificial sequence
<220> FEATURE:
<223> OTHER INFORMATION: Phosphorylation motif

<400> SEQUENCE: 64

```
Met Val Glu Pro Leu Thr Pro Ser Phe
1               5
```

```
<210> SEQ ID NO 65
<211> LENGTH: 9
<212> TYPE: PRT
<213> ORGANISM: Artificial sequence
<220> FEATURE:
<223> OTHER INFORMATION: Phosphorylation motif

<400> SEQUENCE: 65

Met Thr Gly Pro Leu Ser Pro Gly Phe
1               5

<210> SEQ ID NO 66
<211> LENGTH: 9
<212> TYPE: PRT
<213> ORGANISM: Artificial sequence
<220> FEATURE:
<223> OTHER INFORMATION: Phosphorylation motif

<400> SEQUENCE: 66

Met Thr Gly Pro Leu Ser Pro Gly Tyr
1               5

<210> SEQ ID NO 67
<211> LENGTH: 9
<212> TYPE: PRT
<213> ORGANISM: Artificial sequence
<220> FEATURE:
<223> OTHER INFORMATION: Phosphorylation motif

<400> SEQUENCE: 67

Met Thr Gly Pro Leu Ser Pro Gly Leu
1               5

<210> SEQ ID NO 68
<211> LENGTH: 9
<212> TYPE: PRT
<213> ORGANISM: Artificial sequence
<220> FEATURE:
<223> OTHER INFORMATION: Phosphorylation motif

<400> SEQUENCE: 68

Met Thr Gly Pro Leu Ser Pro Gly Pro
1               5

<210> SEQ ID NO 69
<211> LENGTH: 190
<212> TYPE: DNA
<213> ORGANISM: Artificial sequence
<220> FEATURE:
<223> OTHER INFORMATION: FRAGMENT OF pRSET B VECTOR
<220> FEATURE:
<221> NAME/KEY: CDS
<222> LOCATION: (13)..(135)

<400> SEQUENCE: 69
ggagatatac at atg cgg ggt tct cat cat cat cat cat cat ggt atg gct      51
              Met Arg Gly Ser His His His His His His Gly Met Ala
                1               5                  10 agc atg act ggt gga cag caa atg ggt cgg gat ctg tac gac gat gac        99
Ser Met Thr Gly Gly Gln Gln Met Gly Arg Asp Leu Tyr Asp Asp Asp
    15                  20                  25 gat aag gat ccc ccc gct gaa ttc atg agt tac aaa taataaggat            145
Asp Lys Asp Pro Pro Ala Glu Phe Met Ser Tyr Lys
30                  35                  40 ccgagctcga gatctgcagc tggtaccatg gaattcgaag gttga                      190
```

```
<210> SEQ ID NO 70
<211> LENGTH: 41
<212> TYPE: PRT
<213> ORGANISM: Artificial sequence
<220> FEATURE:
<223> OTHER INFORMATION: FRAGMENT OF pRSET B VECTOR

<400> SEQUENCE: 70

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Pro Pro Ala Glu Phe Met Ser Tyr Lys
        35                  40

<210> SEQ ID NO 71
<211> LENGTH: 167
<212> TYPE: DNA
<213> ORGANISM: Artificial sequence
<220> FEATURE:
<223> OTHER INFORMATION: FRAGMENT OF pRSET B VECTOR
<220> FEATURE:
<221> NAME/KEY: CDS
<222> LOCATION: (13)..(69)

<400> SEQUENCE: 71
ggagatatac at atg cgg ggt tct cat cat cat cat cat cat ggt atg gct     51
              Met Arg Gly Ser His His His His His His Gly Met Ala
              1               5                   10 agc atg act ggt gga cag caaatgggtc gggatctgta cgacgatgac              99
Ser Met Thr Gly Gly Gln
            15 gataaggatc cgagctcgag atctgcagct ggtaccatga aagaagaag atcaaaataa     159 aagcttga                                                             167

<210> SEQ ID NO 72
<211> LENGTH: 19
<212> TYPE: PRT
<213> ORGANISM: Artificial sequence
<220> FEATURE:
<223> OTHER INFORMATION: FRAGMENT OF pRSET B VECTOR

<400> SEQUENCE: 72

Met Arg Gly Ser His His His His His His Gly Met Ala Ser Met Thr
1               5                   10                  15

Gly Gly Gln

<210> SEQ ID NO 73
<211> LENGTH: 717
<212> TYPE: DNA
<213> ORGANISM: Aequorea green fluorescent protein phosphorylation
      mutant
<220> FEATURE:
<221> NAME/KEY: CDS
<222> LOCATION: (1)..(714)

<400> SEQUENCE: 73 atg agt aaa gga gaa gaa ctt ttc act gga gtt gtc cca att ctt gtt       48
Met Ser Lys Gly Glu Glu Leu Phe Thr Gly Val Val Pro Ile Leu Val
1               5                   10                  15 gaa tta gat ggt gat gtt aat ggg cac aaa ttt tct gtc agt gga gag       96
Glu Leu Asp Gly Asp Val Asn Gly His Lys Phe Ser Val Ser Gly Glu
            20                  25                  30
```

-continued

```
ggt gaa ggt gat gca aca tac gga aaa ctt acc ctt aaa ttt att tgc        144
Gly Glu Gly Asp Ala Thr Tyr Gly Lys Leu Thr Leu Lys Phe Ile Cys
         35                  40                  45 act act gga aaa cta cct gtt cca tgg cca aca ctt gtc act act ttc        192
Thr Thr Gly Lys Leu Pro Val Pro Trp Pro Thr Leu Val Thr Thr Phe
 50                  55                  60 tct tat ggt gtt caa tgc ttt tca aga tac cca gat cat atg aaa cag        240
Ser Tyr Gly Val Gln Cys Phe Ser Arg Tyr Pro Asp His Met Lys Gln
 65                  70                  75                  80 cat gac ttt ttc aag agt gcc atg ccc gaa ggt tat gta cag gaa aga        288
His Asp Phe Phe Lys Ser Ala Met Pro Glu Gly Tyr Val Gln Glu Arg
                 85                  90                  95 tct ata ttt ttc aaa gat gac ggg aac tac aag aca cgt gct gaa gtc        336
Ser Ile Phe Phe Lys Asp Asp Gly Asn Tyr Lys Thr Arg Ala Glu Val
                100                 105                 110 aag ttt gaa ggt gat acc ctt gtt aat aga atc gag tta aaa ggt att        384
Lys Phe Glu Gly Asp Thr Leu Val Asn Arg Ile Glu Leu Lys Gly Ile
            115                 120                 125 gat ttt aaa gaa gat gga aac att ctt gga cac aaa ttg gaa tac aac        432
Asp Phe Lys Glu Asp Gly Asn Ile Leu Gly His Lys Leu Glu Tyr Asn
130                 135                 140 tat aac tca cac aat gta tac atc atg gca gac aaa caa aag aat gga        480
Tyr Asn Ser His Asn Val Tyr Ile Met Ala Asp Lys Gln Lys Asn Gly
145                 150                 155                 160 atc aaa gtt aac ttc aaa att aga cac aac att gaa gat gga agc gtt        528
Ile Lys Val Asn Phe Lys Ile Arg His Asn Ile Glu Asp Gly Ser Val
                165                 170                 175 caa cta gca gac cat tat caa caa aat act cca att ggc gat ggc cct        576
Gln Leu Ala Asp His Tyr Gln Gln Asn Thr Pro Ile Gly Asp Gly Pro
            180                 185                 190 gtc ctt tta cca gac aac cat tac ctg tcc aca caa tct gcc ctt tcg        624
Val Leu Leu Pro Asp Asn His Tyr Leu Ser Thr Gln Ser Ala Leu Ser
        195                 200                 205 aaa gat ccc aac gaa aag aga gac cac atg gtc ctt ctt gag ttt gta        672
Lys Asp Pro Asn Glu Lys Arg Asp His Met Val Leu Leu Glu Phe Val
210                 215                 220 aca gct gct ggg att aca cat ggc atg gat gaa cta tac aaa taa           717
Thr Ala Ala Gly Ile Thr His Gly Met Asp Glu Leu Tyr Lys
225                 230                 235
```

<210> SEQ ID NO 74
<211> LENGTH: 238
<212> TYPE: PRT
<213> ORGANISM: Aequorea green fluorescent protein phosphorylation mutant

<400> SEQUENCE: 74

```
Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
             35                  40                  45

Thr Thr Gly Lys Leu Pro Val Pro Trp Pro Thr Leu Val Thr Thr Phe
 50                  55                  60

Ser Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95
```

-continued

```
Thr Ile Phe Phe Lys Asp Asp Gly Asn Tyr Lys Thr Arg Ala Glu Val
            100             105             110

Lys Phe Glu Gly Asp Thr Leu Val Asn Arg Ile Glu Leu Lys Gly Ile
        115             120             125

Asp Phe Lys Glu Asp Gly Asn Ile Leu Gly His Lys Leu Glu Tyr Asn
    130             135             140

Tyr Asn Ser His Asn Val Tyr Ile Met Ala Asp Lys Gln Lys Asn Gly
145             150             155             160

Ile Lys Val Asn Phe Lys Ile Arg His Asn Ile Glu Asp Gly Ser Val
                165             170             175

Gln Leu Ala Asp His Tyr Gln Gln Asn Thr Pro Ile Gly Asp Gly Pro
            180             185             190

Val Leu Leu Pro Asp Asn His Tyr Leu Ser Thr Gln Ser Ala Leu Ser
        195             200             205

Lys Asp Pro Asn Glu Lys Arg Asp His Met Val Leu Leu Glu Phe Val
    210             215             220

Thr Ala Ala Gly Ile Thr His Gly Met Asp Glu Leu Tyr Lys
225             230             235
```